(12) United States Patent
Sweeney et al.

(10) Patent No.: US 11,779,238 B2
(45) Date of Patent: Oct. 10, 2023

(54) IMPLANTABLE SENSORS FOR VASCULAR MONITORING

(71) Applicant: Foundry Innovation & Research 1, Ltd., Dublin (IE)

(72) Inventors: Fiachra M. Sweeney, Dublin (IE); Hanson S. Gifford, III, Woodside, CA (US); Douglas S. Sutton, Pacifica, CA (US); Brian Wilfley, Sunnyvale, CA (US); Edward McKenna, Sebastapool, CA (US); Xuance Zhou, Newark, CA (US); Peter Callas, Castro Valley, CA (US); Danyang Fan, Palo Alto, CA (US)

(73) Assignee: Foundry Innovation & Research 1, Ltd., Dublin (IE)

( * ) Notice: Subject to any disclaimer, the term of this patent is extended or adjusted under 35 U.S.C. 154(b) by 685 days.

(21) Appl. No.: 16/618,304

(22) PCT Filed: May 31, 2018

(86) PCT No.: PCT/EP2018/064386
§ 371 (c)(1),
(2) Date: Nov. 29, 2019

(87) PCT Pub. No.: WO2018/220146
PCT Pub. Date: Dec. 6, 2018

(65) Prior Publication Data
US 2020/0129087 A1    Apr. 30, 2020

Related U.S. Application Data

(60) Provisional application No. 62/512,992, filed on May 31, 2017.

(51) Int. Cl.
*A61B 5/0538* (2021.01)
*A61B 5/107* (2006.01)
*A61B 5/00* (2006.01)

(52) U.S. Cl.
CPC .......... *A61B 5/0538* (2013.01); *A61B 5/1076* (2013.01); *A61B 5/6862* (2013.01); *A61B 5/6876* (2013.01); *A61B 5/6886* (2013.01)

(58) Field of Classification Search
CPC ... A61B 5/0538; A61B 5/1076; A61B 5/6862; A61B 5/6876; A61B 5/6886
See application file for complete search history.

(56) References Cited

U.S. PATENT DOCUMENTS

| | | |
|---|---|---|
| 3,568,661 A | 3/1971 | Franklin |
| 4,142,412 A | 3/1979 | McLeod |

(Continued)

FOREIGN PATENT DOCUMENTS

| | | |
|---|---|---|
| DE | 102005035022 A1 | 11/2006 |
| EP | 0399059 A1 | 5/1989 |

(Continued)

OTHER PUBLICATIONS

International Search Report and Written Opinion dated Oct. 19, 2017, in connection with PCT/US2017/046204.

(Continued)

*Primary Examiner* — Kaylee R Wilson
*Assistant Examiner* — Raymond P Dulman
(74) *Attorney, Agent, or Firm* — Downs Rachlin Martin PLLC

(57) ABSTRACT

An implantable sensor for implantation in a vessel, comprising a plurality of electrodes for placement on, in or adjacent a vessel wall, means for providing a drive signal to the electrodes, means for measuring at least one of impedance and capacitance between at least two of the plurality of (Continued)

electrodes, and means for wirelessly communicating data from the sensor and a blood vessel monitoring system comprising same.

1 Claim, 14 Drawing Sheets

(56) References Cited

U.S. PATENT DOCUMENTS

| | | |
|---|---|---|
| 4,638,252 A | 1/1987 | Bradshaw |
| RE32,361 E | 2/1987 | Duggan |
| 4,733,669 A | 3/1988 | Segal |
| 4,926,875 A | 5/1990 | Rabinovitz et al. |
| 4,947,852 A | 8/1990 | Nassi et al. |
| 5,127,404 A | 7/1992 | Wyborny et al. |
| 5,205,292 A | 4/1993 | Czar et al. |
| 5,316,001 A | 5/1994 | Ferek-Petric et al. |
| 5,339,816 A | 8/1994 | Akamatsu et al. |
| 5,495,852 A | 3/1996 | Stadler et al. |
| 5,630,836 A | 5/1997 | Prem et al. |
| 5,752,522 A | 5/1998 | Murphy |
| 5,872,520 A | 2/1999 | Siefert et al. |
| 5,902,308 A | 5/1999 | Murphy |
| 5,967,986 A | 10/1999 | Cimochowski |
| 5,971,933 A * | 10/1999 | Gopakumaran ....... A61B 5/029 600/526 |
| 6,010,511 A | 1/2000 | Murphy |
| 6,012,457 A | 1/2000 | Lesh |
| 6,015,386 A | 1/2000 | Kensey et al. |
| 6,015,387 A | 1/2000 | Schwartz et al. |
| 6,025,725 A | 2/2000 | Gershenfeld et al. |
| 6,039,701 A | 3/2000 | Sliwa et al. |
| 6,053,873 A | 4/2000 | Govari et al. |
| 6,111,520 A | 8/2000 | Allen et al. |
| 6,115,633 A | 9/2000 | Lang et al. |
| 6,115,636 A | 9/2000 | Ryan |
| 6,164,283 A | 12/2000 | Lesh |
| 6,206,835 B1 | 3/2001 | Spillman, Jr. et al. |
| 6,231,516 B1 | 5/2001 | Keilman et al. |
| 6,261,233 B1 | 7/2001 | Kantorovich |
| 6,278,379 B1 | 8/2001 | Allen et al. |
| 6,287,253 B1 | 9/2001 | Ortega et al. |
| 6,325,762 B1 | 12/2001 | Tjin |
| 6,339,816 B1 | 1/2002 | Bausch |
| 6,354,999 B1 | 3/2002 | Dgany et al. |
| 6,398,734 B1 | 6/2002 | Cimochowski et al. |
| 6,434,411 B1 | 8/2002 | Duret |
| 6,503,202 B1 | 1/2003 | Hossack et al. |
| 6,574,510 B2 | 6/2003 | Von Arx et al. |
| 6,673,020 B2 | 1/2004 | Okada et al. |
| 6,699,186 B1 | 3/2004 | Wolinsky et al. |
| 6,738,671 B2 | 5/2004 | Christophersom et al. |
| 6,776,763 B2 | 8/2004 | Nix |
| 6,802,811 B1 | 10/2004 | Slepian |
| 6,855,115 B2 | 2/2005 | Fonseca |
| 6,895,265 B2 | 5/2005 | Silver |
| 6,926,670 B2 | 8/2005 | Rich et al. |
| 6,972,553 B2 | 12/2005 | Petrovich et al. |
| 7,065,409 B2 | 6/2006 | Mazar |
| 7,077,812 B2 | 7/2006 | Naghavi |
| 7,082,330 B2 | 7/2006 | Stadler et al. |
| 7,147,604 B1 | 12/2006 | Allen |
| 7,149,587 B2 | 12/2006 | Wardle et al. |
| 7,191,013 B1 | 3/2007 | Miranda et al. |
| 7,225,032 B2 | 5/2007 | Schmeling et al. |
| 7,233,821 B2 | 6/2007 | Hettrick |
| 7,236,821 B2 | 6/2007 | Cates et al. |
| 7,245,117 B1 | 7/2007 | Joy |
| 7,284,442 B2 | 10/2007 | Fleischman et al. |
| 7,367,984 B2 | 5/2008 | Kulcinski et al. |
| 7,423,496 B2 | 9/2008 | Scheuermann |
| 7,432,723 B2 | 10/2008 | Ellis |
| 7,439,723 B2 | 10/2008 | Allen |
| 7,444,878 B1 | 11/2008 | Pepples |
| 7,452,334 B2 | 11/2008 | Gianchandani et al. |
| 7,454,244 B2 | 11/2008 | Kassab et al. |
| 7,466,120 B2 | 12/2008 | Miller |
| 7,479,112 B2 | 1/2009 | Sweeney et al. |
| 7,481,771 B2 | 1/2009 | Fonseca |
| 7,492,144 B2 | 2/2009 | Powers |
| 7,498,799 B2 | 3/2009 | Allen |
| 7,550,978 B2 | 6/2009 | Joy |
| 7,574,792 B2 | 8/2009 | O'Brien |
| 7,595,647 B2 | 9/2009 | Kroh |
| 7,618,363 B2 | 11/2009 | Yadav |
| 7,621,036 B2 | 11/2009 | Cros |
| 7,621,876 B2 | 11/2009 | Hoctor et al. |
| 7,647,831 B2 | 1/2010 | Corcoran |
| 7,647,836 B2 | 1/2010 | O'Brien |
| 7,662,653 B2 | 2/2010 | O'Brien |
| 7,667,547 B2 | 2/2010 | Ellis |
| 7,677,107 B2 | 3/2010 | Nunez |
| 7,678,135 B2 | 3/2010 | Maahs et al. |
| 7,679,355 B2 | 3/2010 | Allen |
| 7,699,059 B2 | 4/2010 | Fonseca |
| 7,710,103 B2 | 5/2010 | Powers |
| 7,725,160 B2 | 5/2010 | Weber |
| 7,748,277 B2 | 7/2010 | O'Brien |
| 7,778,684 B2 | 8/2010 | Weber et al. |
| 7,786,867 B2 | 8/2010 | Hamel et al. |
| 7,812,416 B2 | 10/2010 | Courcimault |
| 7,829,363 B2 | 11/2010 | You |
| 7,839,153 B2 | 11/2010 | Joy |
| 7,848,813 B2 | 12/2010 | Bergelson et al. |
| 7,854,172 B2 | 12/2010 | O'Brien |
| 7,908,002 B2 | 3/2011 | Hoijer |
| 7,908,018 B2 | 3/2011 | O'Brien |
| 7,909,770 B2 | 3/2011 | Stern |
| 7,932,732 B2 | 4/2011 | Ellis |
| 7,936,174 B2 | 5/2011 | Ellis |
| 7,955,269 B2 | 6/2011 | Stahmann |
| 7,966,886 B2 | 6/2011 | Corcoran |
| 7,988,719 B2 | 8/2011 | Alt et al. |
| 8,016,766 B2 | 9/2011 | Goedje et al. |
| 8,021,307 B2 | 9/2011 | White |
| 8,025,625 B2 | 9/2011 | Allen |
| 8,026,729 B2 | 9/2011 | Kroh |
| 8,060,214 B2 | 11/2011 | Larson et al. |
| 8,078,274 B2 | 12/2011 | Kassab |
| 8,082,032 B2 | 12/2011 | Kassab et al. |
| 8,099,161 B2 | 1/2012 | Kassab |
| 8,107,248 B2 | 1/2012 | Shin et al. |
| 8,111,150 B2 | 2/2012 | Miller |
| 8,114,143 B2 | 2/2012 | Kassab et al. |
| 8,118,749 B2 | 2/2012 | White |
| 8,154,389 B2 | 4/2012 | Rowland |
| 8,159,348 B2 | 4/2012 | Ellis |
| 8,185,194 B2 | 5/2012 | Kassab |
| 8,209,033 B2 | 6/2012 | Zhang et al. |
| 8,221,405 B2 | 7/2012 | Whisenant et al. |
| 8,237,451 B2 | 8/2012 | Joy |
| 8,264,240 B2 | 9/2012 | Park |
| 8,267,954 B2 | 9/2012 | Decant, Jr. et al. |
| 8,278,941 B2 | 10/2012 | Kroh |
| 8,298,147 B2 | 10/2012 | Huennekens et al. |
| 8,298,148 B2 | 10/2012 | Furman |
| 8,353,841 B2 | 1/2013 | White |
| 8,355,777 B2 | 1/2013 | White |
| 8,356,399 B2 | 1/2013 | Kaplan |
| 8,360,984 B2 | 1/2013 | Yadar |
| 8,374,689 B2 | 2/2013 | Gopinathan et al. |
| 8,432,265 B2 | 4/2013 | Rowland |
| 8,442,639 B2 | 5/2013 | Walker et al. |
| 8,465,436 B2 | 6/2013 | Griswold |
| 8,465,452 B2 | 6/2013 | Kassab |
| 8,467,854 B2 | 6/2013 | Lewis et al. |
| 8,493,187 B2 | 7/2013 | Rowland |
| 8,500,660 B2 | 8/2013 | Buchwald et al. |
| 8,521,282 B2 | 8/2013 | Czygan et al. |
| 8,527,046 B2 | 9/2013 | Connelly et al. |
| 8,556,929 B2 | 10/2013 | Harper et al. |
| 8,570,186 B2 | 10/2013 | Nagy |
| 8,600,517 B2 | 12/2013 | Forsell |

(56) References Cited

U.S. PATENT DOCUMENTS

| | | |
|---|---|---|
| 8,613,705 B2 | 12/2013 | Scheurer |
| 8,632,469 B2 | 1/2014 | Kassab |
| 8,644,941 B2 | 2/2014 | Rooney et al. |
| 8,665,086 B2 | 3/2014 | Miner |
| 8,669,770 B2 | 3/2014 | Cros |
| 8,696,584 B2 | 4/2014 | Kassab |
| 8,702,613 B2 | 4/2014 | Kassab |
| 8,706,208 B2 | 4/2014 | Chiao et al. |
| 8,706,209 B2 | 4/2014 | Kassab |
| 8,728,012 B2 | 5/2014 | Braido |
| 8,784,338 B2 | 7/2014 | Wallace |
| 8,798,712 B2 | 8/2014 | Gopinathan et al. |
| 8,814,798 B2 | 8/2014 | Corbucci et al. |
| 8,818,507 B2 | 8/2014 | Liu et al. |
| 8,825,151 B2 | 9/2014 | Gopinathan et al. |
| 8,827,929 B2 | 9/2014 | O'Dea |
| 8,855,783 B2 | 10/2014 | Dagan et al. |
| 8,864,666 B2 | 10/2014 | Kassem |
| 8,870,787 B2 | 10/2014 | Yadav |
| 8,874,203 B2 | 10/2014 | Kassab et al. |
| 8,886,301 B2 | 11/2014 | Kassab |
| 8,894,582 B2 | 11/2014 | Nunez |
| 8,896,324 B2 | 11/2014 | Kroh |
| 8,909,351 B2 | 12/2014 | Dinsmoor et al. |
| 8,918,169 B2 | 12/2014 | Kassab et al. |
| 8,938,292 B2 | 1/2015 | Hettrick et al. |
| 8,951,219 B2 | 2/2015 | Gerber et al. |
| 9,049,995 B2 | 6/2015 | Blomqvist et al. |
| 9,060,798 B2 | 6/2015 | Harper et al. |
| 9,061,099 B2 | 6/2015 | Gerber et al. |
| 9,066,672 B2 | 6/2015 | Kassab et al. |
| 9,198,706 B2 | 12/2015 | Kassab et al. |
| 9,265,428 B2 | 2/2016 | O'Brien et al. |
| 9,289,132 B2 | 3/2016 | Ghaffari et al. |
| 9,289,229 B2 | 3/2016 | Kassab |
| 9,305,456 B2 | 4/2016 | Rowland |
| 9,314,169 B2 | 4/2016 | Kassab |
| 9,326,728 B2 | 5/2016 | Demir et al. |
| 9,332,914 B2 | 5/2016 | Langston |
| 9,332,916 B2 | 5/2016 | Kassab |
| 9,333,365 B2 | 5/2016 | Zhao |
| 9,351,661 B2 | 5/2016 | Kassab |
| 9,393,416 B2 | 7/2016 | Rooney et al. |
| 9,445,743 B2 | 9/2016 | Kassab |
| 9,489,831 B2 | 11/2016 | Nagy et al. |
| 9,526,637 B2 | 12/2016 | Dagan et al. |
| 9,545,263 B2 | 1/2017 | Lenihan et al. |
| 9,603,533 B2 | 3/2017 | Lading et al. |
| 9,662,066 B2 | 5/2017 | Ledet et al. |
| 9,675,257 B2 | 6/2017 | Kassab |
| 9,675,315 B2 | 6/2017 | Song et al. |
| 9,721,463 B2 | 8/2017 | Rowland |
| 9,814,395 B2 | 11/2017 | Stahmann et al. |
| 9,872,948 B2 | 1/2018 | Siess |
| 9,878,080 B2 | 1/2018 | Kaiser et al. |
| 9,901,722 B2 | 2/2018 | Nitzan et al. |
| 9,996,712 B2 | 6/2018 | Sundaram et al. |
| 10,080,528 B2 | 9/2018 | BeBusschere et al. |
| 10,092,247 B2 | 10/2018 | Taylor |
| 10,105,103 B2 | 10/2018 | Goldshtein et al. |
| 10,194,808 B1 | 2/2019 | Thompson |
| 10,195,441 B2 | 2/2019 | Kaiser |
| 10,201,285 B2 | 2/2019 | Sawanoi |
| 10,210,956 B2 | 2/2019 | Lavi |
| 10,213,129 B2 | 2/2019 | Kassab |
| 10,219,704 B2 | 3/2019 | Lavi |
| 10,219,720 B2 | 3/2019 | Kassab |
| 10,219,724 B2 | 3/2019 | Stern |
| 10,226,203 B2 | 3/2019 | Stigall |
| 10,226,218 B2 | 3/2019 | Rowland |
| 10,231,659 B2 | 3/2019 | Vanslyke |
| 10,231,701 B2 | 3/2019 | Ryan |
| 10,236,084 B2 | 3/2019 | Grady |
| 10,238,311 B2 | 3/2019 | Kassab |
| 10,238,322 B2 | 3/2019 | Vanslyke |
| 10,238,323 B2 | 3/2019 | Vanslyke |
| 10,238,324 B2 | 3/2019 | Vanslyke |
| 10,240,994 B1 | 3/2019 | Xu |
| 10,265,024 B2 | 4/2019 | Lee |
| 10,271,797 B2 | 4/2019 | Zhang |
| 10,537,281 B2 | 1/2020 | Thompson et al. |
| 10,542,887 B2 | 1/2020 | Sarkar et al. |
| 10,660,577 B2 | 1/2020 | Thakur et al. |
| 10,548,535 B2 | 2/2020 | Zhang et al. |
| 10,555,704 B2 | 2/2020 | Averina et al. |
| 10,582,866 B2 | 3/2020 | Badie et al. |
| 10,588,528 B2 | 3/2020 | Banet et al. |
| 10,595,734 B2 | 3/2020 | Thakur et al. |
| 10,596,381 B2 | 3/2020 | Averina et al. |
| 10,638,980 B2 | 5/2020 | Gyllensten et al. |
| 10,687,715 B2 | 6/2020 | Jansen et al. |
| 10,702,213 B2 | 7/2020 | Sharma et al. |
| 10,806,352 B2 | 10/2020 | Sweeney et al. |
| 10,905,393 B2 | 2/2021 | Gifford, III et al. |
| 2002/0120205 A1 | 8/2002 | Ferek-Petric |
| 2003/0037591 A1 | 2/2003 | Ashton et al. |
| 2003/0100940 A1 | 5/2003 | Yodfat |
| 2003/0158584 A1 | 8/2003 | Cates et al. |
| 2003/0199938 A1* | 10/2003 | Smits ............... A61B 5/283 607/27 |
| 2004/0054287 A1 | 3/2004 | Stephens |
| 2004/0106871 A1 | 6/2004 | Hunyor et al. |
| 2004/0116992 A1 | 6/2004 | Wardle |
| 2004/0133092 A1 | 7/2004 | Kain |
| 2004/0140939 A1 | 7/2004 | Haller et al. |
| 2004/0167596 A1 | 8/2004 | Richter |
| 2004/0176672 A1* | 9/2004 | Silver ............... A61B 5/14865 600/364 |
| 2004/0215235 A1 | 10/2004 | Jackson et al. |
| 2004/0225326 A1 | 11/2004 | Weiner |
| 2005/0137481 A1 | 6/2005 | Sheard et al. |
| 2005/0148903 A1 | 7/2005 | Diamantopoulos |
| 2005/0154321 A1 | 7/2005 | Wolinsky |
| 2006/0047327 A1 | 3/2006 | Colvin et al. |
| 2006/0056161 A1 | 3/2006 | Shin |
| 2006/0079793 A1 | 4/2006 | Mann et al. |
| 2006/0100522 A1 | 5/2006 | Yuan et al. |
| 2006/0106321 A1 | 5/2006 | Ewinsky et al. |
| 2006/0122522 A1 | 6/2006 | Chavan et al. |
| 2006/0149166 A1 | 7/2006 | Zvuloni |
| 2006/0174712 A1 | 8/2006 | O'Brien |
| 2006/0177956 A1 | 8/2006 | O'Brien |
| 2006/0178695 A1 | 8/2006 | Decant |
| 2006/0253160 A1 | 11/2006 | Benditt et al. |
| 2006/0271119 A1 | 11/2006 | Ni et al. |
| 2006/0287602 A1 | 12/2006 | Obrien et al. |
| 2006/0287700 A1 | 12/2006 | White |
| 2007/0088214 A1 | 4/2007 | Shuros et al. |
| 2007/0129637 A1 | 6/2007 | Wolinsky et al. |
| 2007/0158769 A1 | 7/2007 | You |
| 2007/0199385 A1 | 8/2007 | O'Brien |
| 2007/0249950 A1 | 10/2007 | Piaget et al. |
| 2007/0274565 A1 | 11/2007 | Penner |
| 2007/0282210 A1 | 12/2007 | Stern |
| 2007/0292090 A1 | 12/2007 | Alphonse et al. |
| 2008/0015569 A1 | 1/2008 | Saadat |
| 2008/0033527 A1 | 2/2008 | Nunez et al. |
| 2008/0077016 A1 | 3/2008 | Sparks |
| 2008/0097227 A1 | 4/2008 | Zdeblick et al. |
| 2008/0146946 A1 | 6/2008 | Montegrande et al. |
| 2008/0177186 A1 | 7/2008 | Slater et al. |
| 2008/0294041 A1 | 11/2008 | Kassab |
| 2009/0007679 A1 | 1/2009 | Nunez |
| 2009/0009332 A1 | 1/2009 | Nunez |
| 2009/0011117 A1 | 1/2009 | Nunez |
| 2009/0024042 A1 | 1/2009 | Nunez |
| 2009/0024177 A1 | 1/2009 | Shuros et al. |
| 2009/0030291 A1 | 1/2009 | O'Brien |
| 2009/0062684 A1 | 3/2009 | Gregersen et al. |
| 2009/0105799 A1 | 4/2009 | Hekmat et al. |
| 2009/0149766 A1 | 6/2009 | Shuros et al. |
| 2009/0177225 A1 | 7/2009 | Nunez et al. |
| 2009/0189741 A1 | 7/2009 | Rowland |
| 2009/0198293 A1 | 8/2009 | Cauller |

(56) References Cited

U.S. PATENT DOCUMENTS

| | | |
|---|---|---|
| 2009/0270729 A1 | 10/2009 | Corbucci |
| 2009/0299427 A1 | 12/2009 | Liu et al. |
| 2010/0056922 A1 | 3/2010 | Florent |
| 2010/0063375 A1 | 3/2010 | Kassab et al. |
| 2010/0076398 A1 | 3/2010 | Scheurer et al. |
| 2010/0094328 A1 | 4/2010 | O'dea et al. |
| 2010/0113939 A1 | 5/2010 | Mashimo et al. |
| 2010/0121398 A1 | 5/2010 | Bjorling et al. |
| 2010/0222786 A1 | 9/2010 | Kassab |
| 2010/0262206 A1 | 10/2010 | Zdeblick et al. |
| 2010/0274217 A1 | 10/2010 | Da Silva et al. |
| 2010/0324432 A1 | 12/2010 | Bjorling et al. |
| 2011/0054333 A1 | 3/2011 | Hoffer |
| 2011/0105863 A1 | 5/2011 | Kroh |
| 2011/0144967 A1 | 6/2011 | Adirovich |
| 2011/0160844 A1 | 6/2011 | Taselby |
| 2011/0178383 A1 | 7/2011 | Kassab |
| 2011/0184301 A1 | 7/2011 | Holmstrom et al. |
| 2011/0201990 A1 | 8/2011 | Franano |
| 2011/0224582 A1 | 9/2011 | Spence |
| 2011/0265908 A1 | 11/2011 | Clerc et al. |
| 2011/0306867 A1 | 12/2011 | Gopinathan et al. |
| 2012/0016207 A1 | 1/2012 | Allen |
| 2012/0029598 A1 | 2/2012 | Zhao |
| 2012/0136385 A1 | 5/2012 | Cully |
| 2012/0203090 A1 | 8/2012 | Min |
| 2012/0203113 A1 | 8/2012 | Skerl et al. |
| 2012/0291788 A1 | 11/2012 | Griswold et al. |
| 2012/0296222 A1 | 11/2012 | Griswold et al. |
| 2013/0030295 A1 | 1/2013 | Huennekens et al. |
| 2013/0041244 A1 | 2/2013 | Woias et al. |
| 2013/0041251 A1 | 2/2013 | Bailey et al. |
| 2013/0041269 A1 | 2/2013 | Stahmann et al. |
| 2013/0060139 A1 | 3/2013 | Richter |
| 2013/0073025 A1 | 3/2013 | Kassab |
| 2013/0096409 A1 | 4/2013 | Hiltner et al. |
| 2013/0178750 A1 | 7/2013 | Sheehan et al. |
| 2013/0178751 A1 | 7/2013 | Min |
| 2013/0184545 A1 | 7/2013 | Blomqvist et al. |
| 2013/0218054 A1 | 8/2013 | Sverdlik et al. |
| 2013/0222153 A1 | 8/2013 | Rowland et al. |
| 2013/0245469 A1 | 9/2013 | Yadav |
| 2013/0261655 A1 | 10/2013 | Drasler et al. |
| 2013/0274705 A1 | 10/2013 | Burnes et al. |
| 2013/0281800 A1 | 10/2013 | Saroka et al. |
| 2013/0296721 A1 | 11/2013 | Yadav et al. |
| 2013/0303914 A1 | 11/2013 | Hiltner et al. |
| 2013/0303915 A1 | 11/2013 | Barnard et al. |
| 2013/0310820 A1 | 11/2013 | Fernandez et al. |
| 2013/0317359 A1 | 11/2013 | Wilson et al. |
| 2013/0324866 A1 | 12/2013 | Gladshtein |
| 2013/0331678 A1 | 12/2013 | Lading et al. |
| 2013/0338468 A1 | 12/2013 | Kassab |
| 2014/0028467 A1 | 1/2014 | Nagy |
| 2014/0051965 A1 | 2/2014 | Zdeblick et al. |
| 2014/0066738 A1 | 3/2014 | Kassab |
| 2014/0084943 A1 | 3/2014 | Kroh |
| 2014/0088994 A1 | 3/2014 | Kroh |
| 2014/0094697 A1 | 4/2014 | Petroff et al. |
| 2014/0107768 A1 | 4/2014 | Venkatasubramanian |
| 2014/0155710 A1 | 6/2014 | Rowland |
| 2014/0155768 A1 | 6/2014 | Orion et al. |
| 2014/0155769 A1 | 6/2014 | White |
| 2014/0180118 A1 | 6/2014 | Stigall |
| 2014/0200428 A1 | 7/2014 | Kassab |
| 2014/0236011 A1 | 8/2014 | Fan et al. |
| 2014/0243640 A1 | 8/2014 | O'Dea |
| 2014/0266935 A1 | 9/2014 | Tankiewicz |
| 2014/0275861 A1 | 9/2014 | Kroh |
| 2014/0276011 A1 | 9/2014 | Schmitt et al. |
| 2014/0276067 A1 | 9/2014 | Neasham |
| 2014/0276110 A1 | 9/2014 | Hoseit |
| 2014/0276121 A1 | 9/2014 | Kassab |
| 2014/0276191 A1 | 9/2014 | Kassab |
| 2014/0288085 A1 | 9/2014 | Yadav |
| 2014/0288459 A1 | 9/2014 | Yadav |
| 2014/0306807 A1 | 10/2014 | Rowland |
| 2014/0330143 A1 | 11/2014 | Kroh et al. |
| 2014/0350348 A1 | 11/2014 | Tee et al. |
| 2015/0031966 A1 | 1/2015 | Ward et al. |
| 2015/0045649 A1 | 2/2015 | O'Dea et al. |
| 2015/0051467 A1 | 2/2015 | Corbucci et al. |
| 2015/0065835 A1 | 3/2015 | Kassab |
| 2015/0065897 A1 | 3/2015 | Bornzin et al. |
| 2015/0088100 A1 | 3/2015 | Oborn |
| 2015/0133796 A1 | 5/2015 | Yadav |
| 2015/0141863 A1 | 5/2015 | Kassab et al. |
| 2015/0157268 A1 | 6/2015 | Winshtein et al. |
| 2015/0208929 A1 | 7/2015 | Rowland |
| 2015/0216425 A1 | 8/2015 | Gladshtein et al. |
| 2015/0223702 A1 | 8/2015 | Vanney et al. |
| 2015/0238121 A1 | 8/2015 | Tu et al. |
| 2015/0257732 A1 | 9/2015 | Ryan |
| 2015/0282720 A1 | 10/2015 | Goldshtein et al. |
| 2015/0282875 A1 | 10/2015 | Harper et al. |
| 2015/0290373 A1 | 10/2015 | Rudser et al. |
| 2015/0297110 A1 | 10/2015 | Kassab |
| 2015/0297111 A1 | 10/2015 | Kassab |
| 2015/0297112 A1 | 10/2015 | Kassab et al. |
| 2015/0297113 A1* | 10/2015 | Kassab ............... A61B 5/6847 600/409 |
| 2015/0297818 A1 | 10/2015 | Matsubara et al. |
| 2015/0305808 A1 | 10/2015 | Ku et al. |
| 2015/0313479 A1 | 11/2015 | Stigall et al. |
| 2015/0327786 A1 | 11/2015 | Ading et al. |
| 2016/0000403 A1 | 1/2016 | Vilkomerson |
| 2016/0015507 A1 | 1/2016 | Johnson et al. |
| 2016/0022216 A1 | 1/2016 | Goldshtein et al. |
| 2016/0022447 A1 | 1/2016 | Kim et al. |
| 2016/0029956 A1 | 2/2016 | Rowland |
| 2016/0029995 A1 | 2/2016 | Navratil et al. |
| 2016/0038087 A1 | 2/2016 | Hunter |
| 2016/0045184 A1 | 2/2016 | Courtney |
| 2016/0081657 A1 | 3/2016 | Rice |
| 2016/0095535 A1 | 4/2016 | Hettrick et al. |
| 2016/0135787 A1 | 5/2016 | Anderson et al. |
| 2016/0135941 A1 | 5/2016 | Binmoeller et al. |
| 2016/0166232 A1 | 6/2016 | Merritt |
| 2016/0198981 A1 | 7/2016 | Demir et al. |
| 2016/0210846 A1 | 7/2016 | Rowland et al. |
| 2016/0324443 A1 | 11/2016 | Rowland et al. |
| 2016/0345930 A1 | 12/2016 | Mizukami |
| 2017/0055048 A1 | 2/2017 | Nagy et al. |
| 2017/0055909 A1 | 3/2017 | Schibli et al. |
| 2017/0065186 A1 | 3/2017 | Joseph et al. |
| 2017/0071501 A1 | 3/2017 | Kassab |
| 2017/0127975 A1 | 5/2017 | Bozkurt |
| 2017/0181677 A1* | 6/2017 | Varsavsky ............. A61B 5/0537 |
| 2017/0065824 A1 | 8/2017 | Dagan et al. |
| 2017/0216508 A1 | 8/2017 | Zilbershlag et al. |
| 2017/0238817 A1 | 8/2017 | Lading |
| 2017/0290686 A1 | 10/2017 | Sirhan et al. |
| 2017/0319096 A1 | 11/2017 | Kaiser |
| 2017/0360312 A1 | 12/2017 | Joseph |
| 2018/0014829 A1 | 1/2018 | Tal et al. |
| 2018/0064931 A1 | 3/2018 | Clements |
| 2018/0172785 A1 | 6/2018 | Leussler et al. |
| 2018/0177486 A1 | 6/2018 | Gifford et al. |
| 2018/0220992 A1 | 8/2018 | Gifford et al. |
| 2018/0228951 A1 | 8/2018 | Schwammenthal et al. |
| 2018/0247095 A1 | 8/2018 | Sundaram et al. |
| 2018/0268941 A1 | 9/2018 | Lavi et al. |
| 2018/0269931 A1 | 9/2018 | Hershko et al. |
| 2018/0289488 A1 | 10/2018 | Orth et al. |
| 2018/0289536 A1 | 10/2018 | Burnett |
| 2018/0293409 A1 | 10/2018 | Sundaram et al. |
| 2018/0326151 A1 | 11/2018 | Halpert et al. |
| 2018/0344917 A1 | 12/2018 | Inhaber et al. |
| 2019/0015013 A1 | 1/2019 | Zhu et al. |
| 2019/0029639 A1 | 1/2019 | Gifford et al. |
| 2019/0046047 A1 | 2/2019 | Haase |
| 2019/0053720 A1 | 2/2019 | Sawado |
| 2019/0053767 A1 | 2/2019 | Yamada |
| 2019/0059777 A1 | 2/2019 | Aga et al. |

(56) References Cited

U.S. PATENT DOCUMENTS

| | | |
|---|---|---|
| 2019/0069784 A1 | 3/2019 | Mukkamala |
| 2019/0069842 A1 | 3/2019 | Rothberg |
| 2019/0069851 A1 | 3/2019 | Sharma |
| 2019/0070348 A1 | 3/2019 | Frost |
| 2019/0076033 A1 | 3/2019 | Sweeney et al. |
| 2019/0082978 A1 | 3/2019 | Van der Horst |
| 2019/0083030 A1 | 3/2019 | Thakur |
| 2019/0090760 A1 | 3/2019 | Kinast |
| 2019/0090763 A1 | 3/2019 | Woerlee |
| 2019/0090856 A1 | 3/2019 | Van der Horst |
| 2019/0099087 A1 | 4/2019 | Cros |
| 2019/0099088 A1 | 4/2019 | Whinnett |
| 2019/0110696 A1 | 4/2019 | Benkowski |
| 2019/0126014 A1 | 5/2019 | Kapur et al. |
| 2019/0150884 A1 | 5/2019 | Maharbiz et al. |
| 2019/0167188 A1 | 6/2019 | Gifford et al. |
| 2019/0358393 A1 | 11/2019 | Marbet |
| 2020/0000364 A1 | 1/2020 | Doodeman et al. |
| 2020/0013510 A1 | 1/2020 | Despenic et al. |
| 2020/0022588 A1 | 1/2020 | Wariar et al. |
| 2020/0022589 A1 | 1/2020 | Banet et al. |
| 2020/0029829 A1 | 1/2020 | Banet et al. |
| 2020/0029857 A1 | 1/2020 | Rowland et al. |
| 2020/0030612 A1 | 1/2020 | Song et al. |
| 2020/0037888 A1 | 2/2020 | Thakur et al. |
| 2020/0037892 A1 | 2/2020 | Banet et al. |
| 2020/0046299 A1 | 2/2020 | An et al. |
| 2020/0069857 A1 | 3/2020 | Schwammenthal et al. |
| 2020/0121187 A1 | 4/2020 | Sarkar et al. |
| 2020/0129087 A1 | 4/2020 | Sweeney et al. |
| 2020/0146577 A1 | 5/2020 | Badie et al. |
| 2020/0170515 A1 | 6/2020 | Wen et al. |
| 2020/0170711 A1 | 6/2020 | Hendriks et al. |
| 2020/0187864 A1 | 6/2020 | Sharma |
| 2020/0187865 A1 | 6/2020 | Sharma et al. |
| 2020/0196876 A1 | 6/2020 | Minor et al. |
| 2020/0196899 A1 | 6/2020 | Higgins et al. |
| 2020/0196943 A1 | 6/2020 | Minor et al. |
| 2020/0196944 A1 | 6/2020 | Minor et al. |
| 2020/0196948 A1 | 6/2020 | Cho et al. |
| 2020/0197178 A1 | 6/2020 | Vecchio |
| 2020/0254161 A1 | 8/2020 | Schwammenthal et al. |
| 2020/0289257 A1 | 9/2020 | Marquez |

FOREIGN PATENT DOCUMENTS

| | | |
|---|---|---|
| EP | 0538885 A1 | 4/1993 |
| EP | 0897285 A1 | 2/1999 |
| EP | 1162914 A1 | 12/2001 |
| EP | 1311210 A2 | 5/2003 |
| EP | 0904009 B1 | 9/2003 |
| EP | 1545303 A2 | 6/2005 |
| EP | 1677852 A2 | 7/2006 |
| EP | 1847217 A2 | 10/2007 |
| EP | 1851524 A2 | 11/2007 |
| EP | 1851791 A2 | 11/2007 |
| EP | 1868496 A2 | 12/2007 |
| EP | 1871224 A2 | 1/2008 |
| EP | 1893080 A2 | 3/2008 |
| EP | 1893081 A2 | 3/2008 |
| EP | 1893085 A2 | 3/2008 |
| EP | 2091426 A2 | 6/2008 |
| EP | 1948007 | 7/2008 |
| EP | 1993438 A1 | 11/2008 |
| EP | 2012658 A2 | 1/2009 |
| EP | 2046242 A2 | 4/2009 |
| EP | 2117423 A2 | 11/2009 |
| EP | 2197344 A1 | 6/2010 |
| EP | 2265164 A1 | 12/2010 |
| EP | 2021757 B1 | 4/2011 |
| EP | 2391263 A2 | 12/2011 |
| EP | 1921983 B1 | 1/2012 |
| EP | 2060014 B1 | 1/2012 |
| EP | 1902529 B1 | 6/2012 |
| EP | 1876945 B1 | 12/2012 |
| EP | 2330968 B1 | 4/2013 |
| EP | 2601633 A2 | 6/2013 |
| EP | 2449960 B1 | 10/2013 |
| EP | 2725969 A1 | 5/2014 |
| EP | 1993436 B1 | 6/2014 |
| EP | 3027109 A1 | 2/2015 |
| EP | 2076170 B1 | 4/2015 |
| EP | 2895059 A1 | 7/2015 |
| EP | 2898470 A1 | 7/2015 |
| EP | 2922465 A1 | 9/2015 |
| EP | 2317912 B1 | 11/2015 |
| EP | 1817593 B1 | 12/2015 |
| EP | 2967432 A2 | 1/2016 |
| EP | 2268218 B1 | 2/2016 |
| EP | 2456502 B1 | 4/2016 |
| EP | 2702578 B1 | 8/2016 |
| EP | 3057075 A1 | 8/2016 |
| EP | 2417590 B1 | 5/2017 |
| EP | 2986252 B1 | 7/2018 |
| EP | 3359021 A1 | 8/2018 |
| EP | 3435847 A1 | 2/2019 |
| EP | 3435862 A1 | 2/2019 |
| EP | 3437000 A1 | 2/2019 |
| EP | 3448330 A1 | 3/2019 |
| EP | 3448487 A2 | 3/2019 |
| EP | 3457911 A1 | 3/2019 |
| EP | 3457924 A1 | 3/2019 |
| EP | 3457928 A1 | 3/2019 |
| EP | 3463082 A1 | 4/2019 |
| EP | 3468462 A1 | 4/2019 |
| EP | 3591663 A1 | 1/2020 |
| EP | 3609392 A1 | 2/2020 |
| EP | 3256043 B1 | 3/2020 |
| EP | 3629921 A1 | 4/2020 |
| EP | 3629937 A1 | 4/2020 |
| EP | 3630275 A1 | 4/2020 |
| EP | 3634206 A1 | 4/2020 |
| EP | 3654835 A1 | 5/2020 |
| EP | 3496808 B1 | 6/2020 |
| EP | 2654560 B1 | 7/2020 |
| EP | 3326524 B1 | 7/2020 |
| EP | 3367884 B1 | 7/2020 |
| EP | 3678539 A1 | 7/2020 |
| EP | 3681389 A1 | 7/2020 |
| EP | 3684260 A1 | 7/2020 |
| EP | 3684464 A1 | 7/2020 |
| GB | 2473529 A | 3/2011 |
| WO | 1997042871 A1 | 11/1997 |
| WO | 1998029030 A1 | 12/1997 |
| WO | 1998035611 A1 | 8/1998 |
| WO | 2000055579 A2 | 9/2000 |
| WO | 2000056210 A1 | 9/2000 |
| WO | 2001012092 A1 | 2/2001 |
| WO | 2001013792 A1 | 3/2001 |
| WO | 2002015823 A2 | 2/2002 |
| WO | 2002076289 A2 | 10/2002 |
| WO | 2003061467 A1 | 7/2003 |
| WO | 2003061504 A1 | 7/2003 |
| WO | 2003092495 A1 | 11/2003 |
| WO | 2004014456 A2 | 2/2004 |
| WO | 2004073796 A1 | 9/2004 |
| WO | 2006049796 A2 | 5/2006 |
| WO | 2006086113 A2 | 8/2006 |
| WO | 2006086114 A2 | 8/2006 |
| WO | 2005027998 A2 | 9/2006 |
| WO | 2006094273 A2 | 9/2006 |
| WO | 2006096582 A1 | 9/2006 |
| WO | 2006102905 A1 | 10/2006 |
| WO | 2006110798 A2 | 10/2006 |
| WO | 2007002185 A2 | 1/2007 |
| WO | 2007002224 A2 | 1/2007 |
| WO | 2007002225 A2 | 1/2007 |
| WO | 2007008493 A1 | 1/2007 |
| WO | 2007028035 A2 | 3/2007 |
| WO | 2007035332 A1 | 3/2007 |
| WO | 2007047571 A2 | 4/2007 |
| WO | 2007047794 A2 | 4/2007 |
| WO | 2007061841 A2 | 5/2007 |
| WO | 2007106490 A2 | 9/2007 |

(56) References Cited

FOREIGN PATENT DOCUMENTS

| | | |
|---|---|---|
| WO | 2007106533 A1 | 9/2007 |
| WO | 2007130628 A2 | 11/2007 |
| WO | 2008031011 A1 | 3/2008 |
| WO | 2008031095 A1 | 3/2008 |
| WO | 2008051907 A1 | 5/2008 |
| WO | 2008066569 A2 | 6/2008 |
| WO | 2009006602 A1 | 1/2009 |
| WO | 2009006608 A1 | 1/2009 |
| WO | 2009006610 A1 | 1/2009 |
| WO | 2009006615 A1 | 1/2009 |
| WO | 2009025648 A1 | 2/2009 |
| WO | 2009039174 A1 | 3/2009 |
| WO | 2009111255 A1 | 9/2009 |
| WO | 2009131879 A1 | 10/2009 |
| WO | 2011060359 A2 | 11/2009 |
| WO | 2009146089 A2 | 12/2009 |
| WO | 2009146090 A1 | 12/2009 |
| WO | 2009149462 A2 | 12/2009 |
| WO | 2010011612 A1 | 1/2010 |
| WO | 2010088279 A2 | 8/2010 |
| WO | 2010117597 A1 | 10/2010 |
| WO | 20100117356 A1 | 10/2010 |
| WO | 2011011104 A1 | 1/2011 |
| WO | 2011234884 A | 11/2011 |
| WO | 2012015954 A1 | 2/2012 |
| WO | 2012015955 A1 | 2/2012 |
| WO | 2012019191 A2 | 2/2012 |
| WO | 2012090206 A2 | 7/2012 |
| WO | 2012140147 A3 | 10/2012 |
| WO | 2012145187 A1 | 10/2012 |
| WO | 2012149008 A2 | 11/2012 |
| WO | 2013003754 A1 | 1/2013 |
| WO | 2013142387 A1 | 9/2013 |
| WO | 2014006471 A2 | 1/2014 |
| WO | 2004014456 A2 | 2/2014 |
| WO | 2014047528 A1 | 3/2014 |
| WO | 2014054045 A1 | 4/2014 |
| WO | 2014070316 A1 | 5/2014 |
| WO | 2014076620 A2 | 5/2014 |
| WO | 2014081958 A1 | 5/2014 |
| WO | 2014145531 A1 | 9/2014 |
| WO | 2014145712 A1 | 9/2014 |
| WO | 2014162181 A2 | 10/2014 |
| WO | 2014170771 A1 | 10/2014 |
| WO | 2014179739 A1 | 11/2014 |
| WO | 2014188430 A2 | 11/2014 |
| WO | 2014197101 A1 | 12/2014 |
| WO | 2015074018 A1 | 5/2015 |
| WO | 2015109028 A1 | 7/2015 |
| WO | 20150157712 A2 | 10/2015 |
| WO | 2016011309 A2 | 1/2016 |
| WO | 2016025430 A1 | 2/2016 |
| WO | 2016131020 A1 | 8/2016 |
| WO | 2016178196 A2 | 11/2016 |
| WO | 2016178197 A1 | 11/2016 |
| WO | 2017024051 A1 | 2/2017 |
| WO | 2017143198 A1 | 8/2017 |
| WO | 2017198867 A1 | 11/2017 |
| WO | 2017222964 A1 | 12/2017 |
| WO | 2018013725 A1 | 1/2018 |
| WO | 2018031714 A1 | 2/2018 |
| WO | 2018081314 A1 | 5/2018 |
| WO | 2018102435 A1 | 6/2018 |
| WO | 2018150314 A1 | 8/2018 |
| WO | 2018156930 A1 | 8/2018 |
| WO | 2018187582 A1 | 10/2018 |
| WO | 2018220143 A1 | 12/2018 |
| WO | 2018220146 A1 | 12/2018 |
| WO | 2019050831 A1 | 3/2019 |
| WO | 2019051007 A1 | 3/2019 |
| WO | 2019051108 A1 | 3/2019 |
| WO | 2019051007 A8 | 4/2019 |
| WO | 2019063521 A1 | 4/2019 |
| WO | 2019079364 A1 | 4/2019 |
| WO | 2020023839 A1 | 1/2020 |
| WO | 2020121221 A1 | 6/2020 |
| WO | 2020131247 A1 | 6/2020 |
| WO | 2020132460 A1 | 6/2020 |
| WO | 2020132668 A2 | 6/2020 |
| WO | 2020132669 A1 | 6/2020 |
| WO | 2020132670 A1 | 6/2020 |
| WO | 2020132671 A1 | 6/2020 |
| WO | 2020132678 A1 | 6/2020 |
| WO | 2020144075 A1 | 7/2020 |
| WO | 2020153765 A2 | 7/2020 |

OTHER PUBLICATIONS

Brennan, J.M., "Handcarried Ultrasound Measurement of the Inferior Vena Cava for Assessment of Intravascular Volume Status in the Outpatient Hemodialysis Clinic"; Clinical Journal of the American Society of Nephrology; pp. 749-753; Jan. 23, 2006.

International Search Report and Written Opinion dated Oct. 20, 2016, in connection with PCT/US2016/045385 filed Aug. 3, 2016.

International Search Report and Written Opinion dated Feb. 27, 2020, in connection with PCT/IB2019/060669 filed Dec. 11, 2019.

Extended European Search Report dated Jul. 3, 2020, in connection with EP20163433.4.

Horizon Scanning Research & Intelligence Centre; Furosemide sc2Wear micro-pump patch for oedema in heart failure; National Institute for Health Research; NIHR HSRIC ID: 11808; Mar. 2016; pp. 1-10; www.hsric.nihr.ac.uk.

ISR Report and Written Opinion dated Dec. 30, 2020, in connection with PCT/EP2020/067713 filed on Jun. 24, 2020.

International Search Report and Written Opinion dated Mar. 3, 2020, in connection with PCT/US2019/066589 filed Dec. 16, 2019.

Voroneanu et al., "The relationship between chronic volume overload 3 and elevated blood pressure in hemodialysis patients: 4 use of bioimpedance provides a different perspective 5 from echocardiography and biomarker methodologies," Int Urol Nephrol, Sep. 2010; 42(3):789-97.

Cannesson et al., "Respiratory Variations in Pulse Oximetry Plethysmographic Waveform Amplitude to Predict Fluid Responsiveness in the Operating Room," Anesthesiology 2007; 106:1105-11.

Abraham et al., "The Role of Implantable Hemodynamic Monitors to Manage Heart Failure," Heart Failure Clin 11 (2015) 183-189.

Tallaj et al., "Implantable Hemodynamic Monitors," Cardiol Clin 29 (2011) 289-299.

Tang et al., "Measuring impedance in congestive heart failure: Current options and clinical applications," American Heart Journal 157 (3) 402-411.

Merchant et al., "Implantable Sensors for Heart Failure," Circulation: Arrhythmia and Electrophysiology. 2010; 3: 657-667.

Unadkat, Jignesh V., et al. "The Development of a Wireless Implantable Blood Flow Monitor," Ideas and Innovations, American Society of Plastic Surgeons, 136:199 (2015).

Steinhouse, David et al., "Implant Experience with an Implantable Hemodynamic Monitor for the Management of Symptomatic Heart Failure," PACE (Aug. 2005) vol. 28, pp. 747-753.

Braunschweig, Frieder et al. "Dynamic changes in right ventricular pressures during haemodialysis recorded with an implantable haemodynamic monitor," Nephrol Dial Transplant (2006) 21:176-183.

Karamanoglu, Mustafa et al., "Estimation of cardiac output in patients with congestive heart failure by analysis of right ventricular pressure waveforms," BioMedical Engineering OnLine 2011, 10:36.

Spiliopoulos, Sotirios et la., "Beneficial aspects of real time flow measurements for the management of acute right ventricular heart failure following continuous flow ventricular assist device implantation," Journal of Cardiothoracic Surgery (2012) 7:119.

Sharma, Arjun D. et al., "Right Ventricular Pressure During Ventricular Arrhythmias in Humans: Potential Implications for Implantable Antitachycardia Devices," JACC vol. 15, No. 3, Mar. 1, 1990, pp. 648-655.

(56) References Cited

OTHER PUBLICATIONS

Kjellstrom, Barbo et al., "Changes in Right Ventricular Pressures Between Hemodialysis Sessions Recorded by an Implantable Hemodynamic Monitor," The American Journal of Cardiology, 2009, 103:119-123.

Zile, Michael R. et al., "Transition From Chronic Compensated to Acute Decompensated Heart Failure," Circulation, American Heart Association (2008) 118:1433-1441.

Plicchi, G. et al., "Pea I and Pea II Based Implantable Haemodynamic Monitor: Pre Clinical Studies in Sheep," Europace (2002) 4, 49-54.

Vanderheyden, Marc et al., "Continuous Monitoring of Intrathoracic Impedance and Right Ventricular Pressures in Patients With Heart Failure," Circulation Heart Failure (2010) 3:370-377.

Jacobs, Donald L. et al., "Bedside vena cava filter placement with intravascular ultrasound: A simple, accurate, single venous access method," Technical Note, Journal of Vascular Surgery, vol. 46, No. 6, pp. 1284-1286, Dec. 2007.

Muller, Laurent et al., "Respiratory variations of inferior vena cava diameter to predict fluid responsiveness in spontaneously breathing patients with acute circulatory failure: need for a cautious use," Critical Care 2012, 16:R188.

Blehar, David J. et al., "Identification of congestive heart failure via respiratory variation of inferior vena cava diameter." American Journal of Emergency Medicine (2009) 27, 71-75.

Miller, Joseph B., et al., "Inferior vena cava assessment in the bedside diagnosis of acute heart failure," American Journal of Emergency Medicine (2012) 30, 778-783.

Corl, Keith et al., "Bedside sonographic measurement of the inferior vena cava caval index is a poor predictor of fluid responsiveness in emergency department patients," Emergency Medicine Australasia (2012) 24, 534-539.

Eissel, et al. "The respiratory variation in inferior vena cava diameter as a guide to fluid therapy," Intensive Care Med (2004) 30: 1834-1837.

Nakao, Shoichiro et al., "Effects of Positional Changes on Inferior Vena Caval Size and Dynamics and Correlations with Right-Sided Cardiac Pressure," American Journal of Cardiology (1987; 59:125-132).

Saha, Narayan M., et al., "Outpatient Use of Focused Cardiac Ultrasound to Assess the Inferior Vena Cava in Patients With Heart Failure," American Journal of Cardiology (2015).

Ishizaki, et al. "Measurement of inferior vena cava diameter for evaluation of venous return in subjects on day 10 of a bed-rest experiment," J Appl Physical 96: 2179-2186, 2004.

Carbone et al. "Inferior Vena Cava Parameters Predict Re-admission in Ischaemic Heart Failure", European Journal of Clinical Investigations, 2014, 44(4): 341-349.

Bertram, C.D. et al., "Cross-sectional area measurement in collapsed tubes using the transformer principle", Med. & Biol, Eng. & Comput, 1989, 27, 357-364.

Moreno, Augusto et al., "Mechanics of Distension of Dog Veins and Other Very Thin-Walled Tubular Structures", Circulation Research, vol. XXVII, Dec. 1970, pp. 1069-1080.

Tafur, Emilio et al., "Simultaneous Pressure, Flow and Diameter of the Vena Cava with Fright and Exercise", Circulation Research, vol. XIX, Jul. 1966., pp. 42-50.

Guntheroth, Warren G., et al., "Effect of Respiration on Venous Return and Stroke Volume in Cardiac Tamponade", Circulation Research, vol. XX, Apr. 1967, pp. 381-390.

Bartels, Lambertus et al., "Improved Lumen Visualization in Metallic Vascular Implants by Reducing RF Artifacts", Magnetic Resonance in Medicine 47:171-180 (2002).

Guntheroth, Warren G., "in Vivo Measurement of Dimensions of Veins with Implications Regarding Control of Venous Return", IEEE Transactions on Bio-Medical Engineering, Oct. 1969; pp. 247-253.

Kivelitz, Dietmar et al., "A Vascular Stent as an Active Component for Locally Enhanced Magnetic Resonance Imaging", Investigative Radiology, vol. 38, No. 3, 147-152 (2003).

Reddy, Reddy R.V., et al., "A Catheter-Tip Probe for Dynamic Cross-Section Area Measurement", pp. 149-158. (1973).

Stegall, H. Fred, "Survey of Dimension Transducers", Chronically Implanted Cardiovascular Instrumentation, pp. 107-115 (1973).

D. H. Bergel, "The Measurement of Lengths and Dimensions", Cardiovascular Fluid Dynamics, vol. 1. pp. 91-114 (1972).

Baan, Jan et al., "Dynamic Local Distensibility of Living Arteries and its relation to Wave Transmission", Biophysical Journal, vol. 14, (1974); pp. 343-362.

International Search Report and Written Opinion in connection with PCT/US2016/017902, dated Jul. 27, 2016.

Reems, Miryam et al., Central Venous Pressure: Principles, Measurement, and Interpretation, Vetlearn.com, Jan. 2012, Compendium: Continuing Education for Veterinarians, pp. E1-E10.

Yamauchi, Hideko et al., "Correlation Between Blood Volume and Pulmonary Artery Catheter Measurements", Department of Surgery and Surgical Critical Care, University of Hawaii, 2005.

Abraham, William T. et al., "Wireless pulmonary artery haemodynamic monitoring in chronic heart failure: a randomised controlled trial"; www.thelancet.com, vol. 377, Feb. 19, 2011, pp. 658-666.

Guiotto, Giovanna et al., "Inferior vena cava collapsibility to guide fluid removal in slow continuous ultrafiltration: a pilot study", Intensive Care Med (2010) 36:696-696.

Martens, Pieter et al., "Current Approach to Decongestive Therapy in Acute Heart Failure", Curr Heart Fail Rep (2015) 12:367-378.

Dupont, Matthias et a., "Impact of Systemic Venous Congestion in Heart Failure", Curr Heart Fail Rep (2011) 8:233-241.

Marik, Paul E. et al., "Hemodynamic parameters to guide fluid therapy", Annals of Intensive Care 2011, 1:1; http://www.annalsofintensivecare.com/content/1/1/1.

Silverberg, Donald et al., "The association between congestive heart failure and chronic renal disease", Curr Opin Nephrol Hypertens 13: 163-170, 2004.

International Search Report and Written Opinion dated Mar. 27, 2018, in connection with PCT/US2017/063749.

International Search Report and Written Opinion dated Aug. 29, 2018, in connection with PCT/EP2018/064386.

International Search Report and Written Opinion dated Aug. 21, 2018, in connection with PCT/EP2018/064383.

International Search Report and Written Opinion dated Nov. 4, 2019, in connection with PCT/US2019/034657, filed May 30, 2019.

Extended European Search Report dated Sep. 16, 2020, in connection with EP Application No. 20178613.4, filed Nov. 29, 2017.

\* cited by examiner

25: wall flow
26: mid-vessel flow
27: trans-vessel flow

| 1 | Measured Data (parallelogram) |

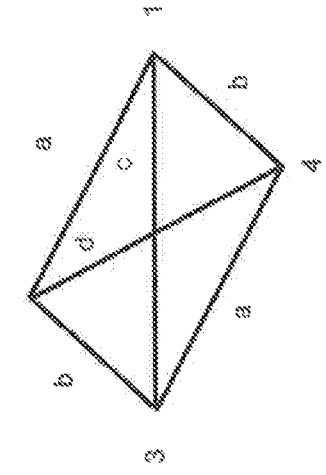

| 2 | Expected Correction (parallelogram) |

| 3 | Parallelogram Edge Correction |

$a=(l_{12}+l_{34})/2$ $b=(l_{23}+l_{14})/2$

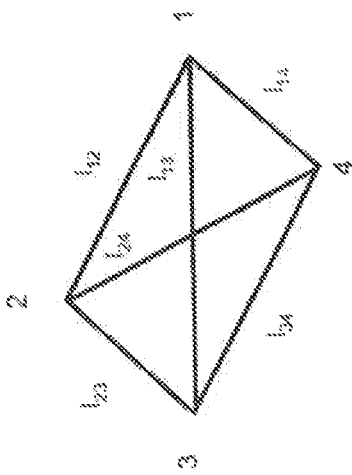

| 4 | Parallelogram Diagonal Correction |

$c = l_{13} + x, \; d = l_{24} + y$ ($x, y$ here are the correction terms)

The correction is reduced to an optimization problem: $\min x^2 + y^2$

S. t. $(l_{13}+x)^2 + (l_{24}+y)^2 = 2(a^2+b^2)$ (Geometric constraint for Parallelogram)

Solving the optimization problem above:

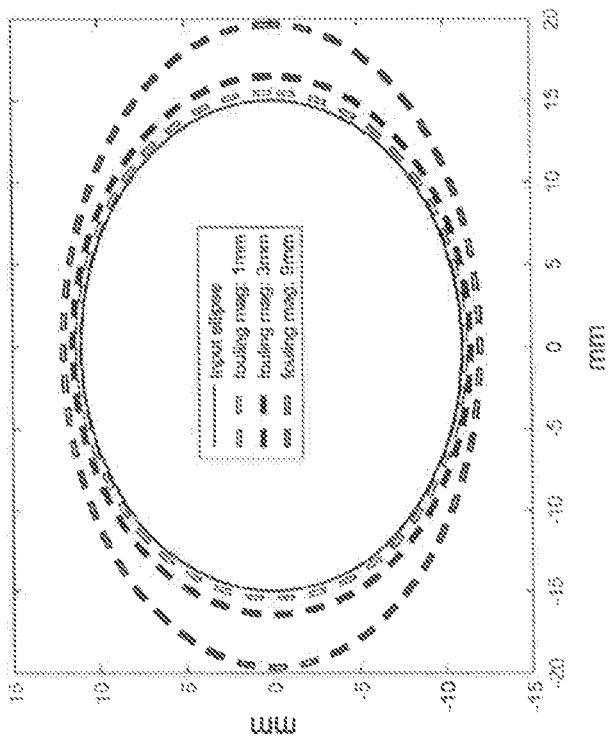
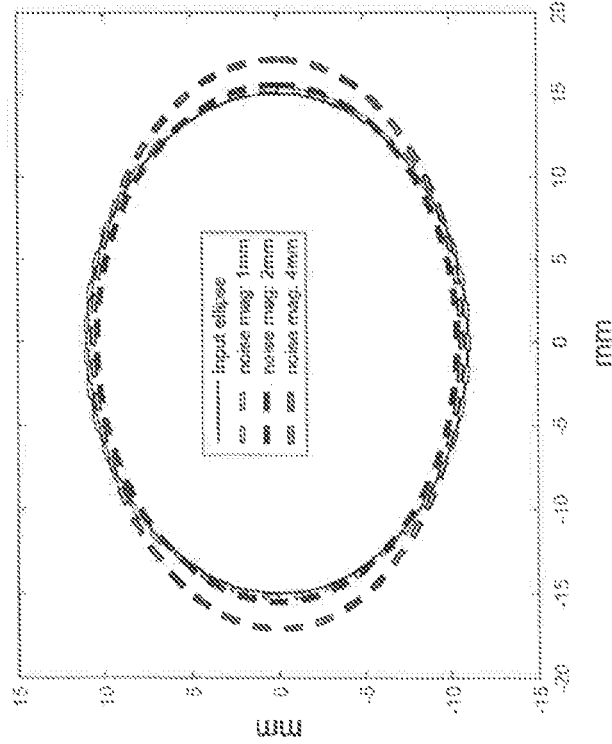
Fig. 14

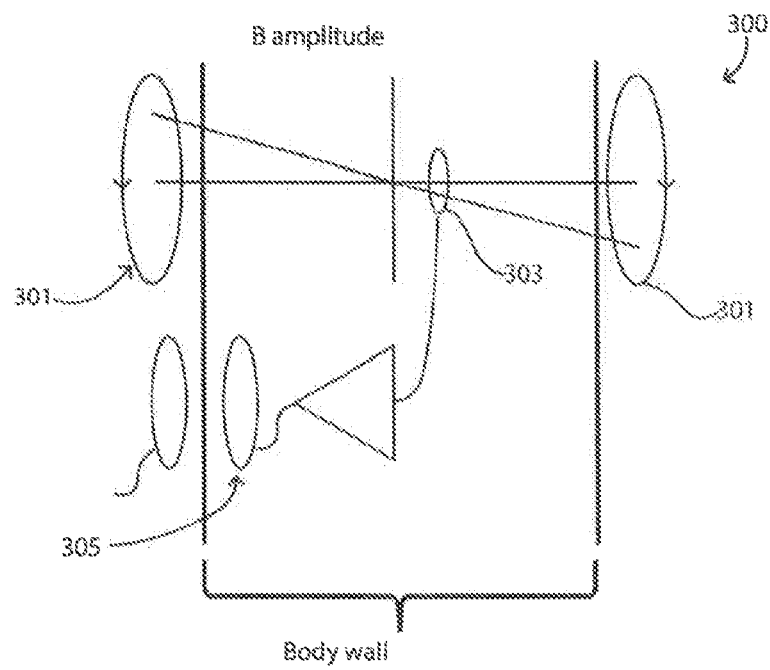
Fig.20
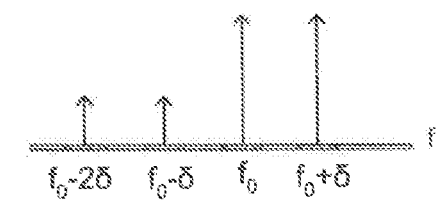
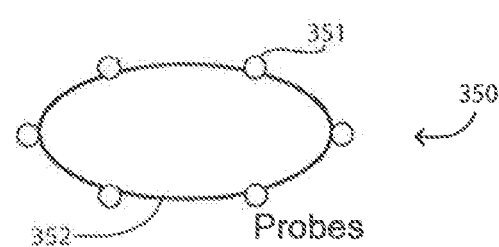
Fig.21

IMPLANTABLE SENSORS FOR VASCULAR MONITORING

RELATED APPLICATIONS

WO2016/131020 and WO2017/024051 are filed by the present Assignee and are incorporated by reference herein in their entirety.

FIELD OF THE DISCLOSURE

The present disclosure generally relates to the field of medical devices and methods for monitoring patient blood vessels (or "vascular lumen"), such as the inferior vena cava ("IVC").

BACKGROUND

Conditions which May be Monitored by IVC or Other Blood Vessel Monitoring

Heart failure is one of the most significant chronic conditions afflicting adult populations. In the United States, 5.7 million Americans have heart failure, with 870,000 new cases annually. As the population ages, this number is growing, as approximately 10% of the population over 80 suffers from heart failure.

In patients with chronic heart failure, significant costs are due to hospitalization to manage acutely decompensated heart failure (ADHF). Each re-hospitalization can last up to a week. ADHF is very often a result of some combination of a downturn in the heart's performance, a downturn in the kidney's removal of fluid from the bloodstream, and/or excessive intake of fluids and/or salt. This leads to a buildup of fluid in the vascular system, resulting in increased blood volume in the left atrium at higher pressure. This eventually leads to fluid filling the lungs and an inability to breathe. Managing these patients to prevent the need for re-hospitalization is extremely challenging. Non-invasive approaches to monitoring patients have been tried, such as weighing patients daily to detect fluid weight gain, or having a nurse call them daily to assess their health status, but these approaches have only modest effectiveness.

Although measurement of left atrial pressure, typically by measuring pulmonary artery wedge pressure, is commonly considered the most direct way to measure congestion in heart failure, there are other areas where congestion can be detected. When additional blood volume is added to the circulatory system, the IVC is one of the first places for that added volume to have an effect. The diameter of the IVC has demonstrated correlation with central venous pressure and right atrial pressure (as a proxy for left atrial pressure) as it flows directly into the right atrium (and by extension left atrial pressure through the connection through the pulmonary circulation), and it may correlate with renal function and renal sodium retention, which are also very important prognostic factors of heart failure. Therefore, increasing IVC volume and/or pressure may be a very effective early indicator of worsening heart condition.

In addition to heart failure patients, hemodialysis patients have a chronic need for careful volume management. Since their kidneys are not excreting fluid, they are constantly becoming overloaded with fluid. Furthermore, large volumes of fluid are involved in the hemodialysis process, and managing patients so that they do not end up hypovolemic or overloaded with fluid requires careful management.

There are other groups of patients who might benefit from such a monitor. For example, patients in septic shock or acute shock due to trauma are subject to hypoperfusion.

Current Approaches to Monitoring the IVC or Other Blood Vessels

Prior studies of IVC dimensions have been conducted using external ultrasound imaging. This typically requires a highly trained physician or ultrasound technician to manage the ultrasound machine, ensure an appropriate connection of the transducer to the skin, position the ultrasound transducer in the appropriate location, identify the IVC, and take accurate measurements. This is not something that heart failure patients or their caregivers could typically be trained to do predictably and accurately with existing equipment. Moreover, these systems typically include large, complex, and expensive pieces of equipment which are not suitable for use outside of a specialized medical facility and are therefore not designed for serial measurements for chronic monitoring purposes.

Recent studies have indicated that the variation in IVC diameter over the respiratory cycle may be a more sensitive measurement of fluid overload and/or heart failure than simple measurement of average IVC diameter, volume, or pressure. During inspiration, intrathoracic pressure decreases, thereby increasing venous return and causing collapse of the IVC. During expiration, intrathoracic pressure increases, decreasing venous return and causing an increase in the diameter of the IVC.

While vessel dimensions may be measurable using external ultrasound, magnetic resonance imaging, computerized axial tomography, or other technologies, these imaging procedures must be administered in a hospital or other specialized facility. Furthermore, such procedures do not permit continuous monitoring and do not allow for monitoring of the patient at their home or other remote location. As a result, the condition of a heart failure patient can worsen into a critical state before care providers become aware of it, dramatically increasing the mortality risk and cost of treatment for the patient.

PCT publication numbers WO2016/131020 and WO2017/024051, assigned to the assignee of the present disclosure, describe approaches involving implanted and catheter-based devices for real time monitoring of IVC dimensions for the diagnosis and treatment of heart failure and other conditions.

The present disclosure is directed towards providing improved apparatus for blood vessel dimension monitoring.

SUMMARY OF THE DISCLOSURE

In accordance with the present invention there is provided an implantable sensor for implantation in a vessel, comprising:
  a plurality of electrodes for placement on, in or adjacent a vessel wall;
  means for providing a drive signal to the electrodes;
  means for measuring at least one of impedance and capacitance between at least two of the plurality of electrodes; and
  means for wirelessly communicating data from the sensor.

The implantable sensor may further comprise means for calculating distance between the electrodes based on the measured impedance or the measured capacitance.

The implantable sensor may further comprise means for estimating vessel diameter based on measurements of impedance or capacitance between at least two of the plurality of electrodes.

The implantable sensor may further comprise means for determining cross-sectional area of the vessel's lumen based on said impedance or capacitance.

The implantable sensor may further comprise means for selecting a pair of electrodes from the plurality of electrodes to which drive signals are to be delivered.

The implantable sensor may further comprise means for estimating blood velocity from the calculated distance between the electrodes.

The implantable sensor may further comprise means for estimating a pressure gradient from the calculated distance between the electrodes.

The implantable sensor may further comprise at least one reference electrode maintained at a fixed distance from one of the electrodes and means for measuring at least one of impedance or capacitance between said electrode and said reference electrode.

The implantable sensor may further comprise means for calibrating measurements between the plurality of electrodes using a measurement of impedance or capacitance between said electrode and said reference electrode.

The implantable sensor may further comprise means for processing the measured electrical parameter to monitor variations in the conductivity of the intervening media and to apply a correction factor accordingly.

The implantable sensor may further comprise means for wirelessly communicating data from the sensor, the means being configured to wirelessly communicate the measured impedance and/or capacitance.

The implantable sensor may further comprise a memory for storing the measurements.

The implantable sensor may further comprise processing means for processing the measured data.

The implantable sensor may further comprise means for wirelessly receiving data from a remote transmitter.

The implantable sensor may further comprise means for biasing the plurality of electrodes against the vessel wall.

The plurality of electrodes may be anchorable to or within the vessel wall.

The plurality of electrodes may comprise a circumferential array of electrodes.

The plurality of electrodes may comprise a plurality of pairs of electrodes.

The implantable sensor may further comprise a support structure with sufficient elasticity to collapse and expand with the vessel without constraining the vessel's natural physiological shape changes, on which the electrodes are mounted. In other words, in use, the electrodes move with the vessel wall. A movement of the vessel wall in a radial direction would impart a corresponding movement of the electrodes in a radial direction.

The implantable sensor may further comprise a support structure having an anchored part configured to engage the vessel wall and wherein each electrode is coupled to the support structure by a connecting strut extending from the anchored part of the support structure, the connecting strut being configured to bias the electrode into engagement with the vessel wall. In some embodiments each electrode is coupled to the inside of a connecting strut. This is an example of each electrode being placeable on the vessel wall. In other embodiments each electrode is coupled to the outside of a connecting strut. This is an example of each electrode being placeable adjacent the vessel wall.

The at least one connecting strut may be cantilevered from the anchored part of the support structure.

The support structure may comprise a stent-like flexible, elastic, cylindrical structure comprised of a slotted tube, interconnecting struts, or mesh, and/or having a continuous zig-zag or sinusoidal geometry.

The at least one strut may comprise an anchor for engagement directly with a vessel wall.

At least part of the sensor may be configured to endothelialize on a vessel wall. This is an example of each electrode being placeable in the vessel wall.

At least one electrode may have an anti-fouling surface to prevent endothelialization on a vessel wall.

The anti-fouling surface may include one or more material selected from carbon nanotubes, conductive polymers, hydrogels, conductive hydrogels, bioactive coatings, and a tissue engineered neural interface.

The implantable sensor may be configured for untethered retention in a vessel. In other words, there is no catheter attached to the implant after implantation.

The implantable sensor may be configured for retention in a vessel following withdrawal of a deployment catheter.

The implantable sensor may further comprise means for executing an algorithm to reduce effects of fouling and/or endothelialisation on electrode surfaces.

The algorithm may include one or more of the steps of performing impedance-to-distance calibration based on resting dimensions; salinity recalibration with scales impedance measurements with reference change, geometric reconstruction with elliptical assumption, fouling detection and rejection according to electrode geometry, preferably with data from three or more electrodes to reconstruct an ellipse, additional data used to detect and reject fouling.

The implantable sensor may further comprise means for performing data correction with parallelogram edge and diagonal correction, by averaging opposed parallelogram sides.

The implantable sensor may further comprise means for performing ellipse reconstruction to model a vessel shape, based on chordal lengths such as parallelogram side calculations.

The implantable sensor may further comprise means for applying a correction to compensate for change from a round to elliptical cross-sectional shape of the vessel.

The implantable sensor may further comprise means for comparing a parameter between multiple pairs of electrodes.

The implantable sensor may further comprise means for determining a pair of electrodes which is most closely aligned with a selected axis of the vessel.

The implantable sensor may be adapted to determine vessel collapsibility or deformity over at least one respiratory cycle.

The implantable sensor may further comprise at least one radiation-detectable marker and/or physical features to allow deployment with at least one pair of electrodes separated in an anterior-posterior dimension.

The means for providing a drive signal may be configured to deliver a sinusoidal waveform and the sensor further comprises means for cycling through each electrode pair taking impedance measurements or capacitive measurements.

The implantable sensor may further comprise means for performing an impedance to distance calibration based on initial resting dimensions of the electrodes, and to perform a geometric reconstruction based on the assumption that the blood vessel has an elliptical shape.

At least two electrodes may be spaced apart in the longitudinal direction of the vessel.

The implantable sensor may further comprise means for processing data from the electrodes on the basis of impedance planimetry.

The implantable sensor may further comprise means for applying an alternating current, AC, across an outer pair of the plurality of electrodes.

The implantable sensor may further comprise means for measuring AC voltage between an inner pair of the plurality of electrodes, the inner pair positioned between the outer pair of electrodes.

In accordance with the present invention there is further provided a blood vessel monitoring system comprising at least one implantable sensor of any preceding claim, and a remote processor configured to receive the communicated data and calculate distance between the electrodes based on the measured impedance or the measured capacitance.

The remote processor may be further configured to estimate vessel diameter based on measurements of impedance and capacitance between at least two of the plurality of electrodes.

The remote processor may be further configured to determine cross-sectional area at a mid-point between said electrodes.

The remote processor may be further configured to select a pair of electrodes from the plurality of electrodes to which drive signals are to be delivered.

The remote processor may be further configured to estimate blood velocity from the calculated distance between the electrodes.

The remote processor may be further configured to estimate a pressure gradient from the calculated distance between the electrodes.

In accordance with the present invention there is further provided a blood vessel monitoring system comprising:
- a plurality of implantable electromagnetic beacon transponders for placement in a blood vessel, on, adjacent or in a blood vessel wall, the transponders adapted to emit a signal when excited;
- an electromagnetic source for exciting the transponders; and
- a sensing array to receive emitted signals and monitor relative positions of the implanted transponders.

The sensor array may be configured to detect a resonant frequency of each transponder to differentiate the transponders.

The blood vessel monitoring system may further comprise means for determining a cross sectional area of the vessel.

The blood vessel monitoring system may further comprise means for determining the blood vessel diameter based on the relative positions of the implanted transponders.

In accordance with the present invention there is further provided an implantable sensor for implantation in a vessel, comprising:
- a plurality of electromagnetic beacon transponders for placement on, adjacent or in a vessel wall, the electromagnetic beacon transponders adapted to emit a signal when excited by electromagnetic radiation.

The implantable sensor may further comprise a battery power source.

The implantable sensor may further comprise a data processing subsystem.

The implantable sensor may further comprise a communications subsystem.

In accordance with the present invention there is further provided a vascular monitoring method comprising:
- implanting a plurality of electrodes within a vessel, on, in or adjacent a vessel wall;
- providing a drive signal to the electrodes;
- measuring at least one of impedance and capacitance between at least two of the plurality of electrodes; and
- wirelessly communicating data from within the vessel.

The method may further comprise calculating the distance between the electrodes based on the measured impedance or the measured capacitance.

The method may further comprise estimating vessel diameter based on measurements of impedance or capacitance between at least two of the plurality of electrodes.

The method may further comprise determining cross-sectional area of the vessel's lumen based on said impedance or capacitance.

The method may further comprise selecting a pair of electrodes from the plurality of electrodes and delivering drive signals to the selected pair.

The method may further comprise estimating blood velocity from the calculated distance between the electrodes.

The method may further comprise estimating a pressure gradient from the calculated distance between the electrodes.

The method may further comprise maintaining at least one reference electrode at a fixed distance from one of the electrodes and measuring at least one of impedance or capacitance between said electrode and said reference electrode.

The method may further comprise calibrating measurements between the plurality of electrodes using a measurement of impedance or capacitance between said electrode and said reference electrode.

The method may further comprise processing the measured electrical parameter to monitor variations in the conductivity of the intervening media and to apply a correction factor accordingly.

The method may further comprise wirelessly communicating the measured impedance and/or capacitance.

The method may further comprise storing the measurements.

The method may further comprise processing the measured data.

The method may further comprise wirelessly receiving data from a remote transmitter.

The method may further comprise executing an algorithm to correct the measurements for effects of fouling and/or endothelialisation on electrode surfaces.

Executing the algorithm may include one or more of the steps of performing impedance-to-distance calibration based on resting dimensions; salinity recalibration with scales impedance, measurements with reference change, geometric reconstruction with elliptical assumption, fouling detection and rejection according to electrode geometry, preferably with data from three or more electrodes to reconstruct an ellipse, additional data used to detect and reject fouling.

The method may further comprise performing data correction with parallelogram edge and diagonal correction, by averaging opposed parallelogram sides.

The method may further comprise performing ellipse reconstruction to model a vessel shape, based on chordal lengths such as parallelogram side calculations.

The method may further comprise applying a correction to compensate for change from a round to elliptical cross-sectional shape of the vessel.

The method may further comprise comparing a parameter between multiple pairs of electrodes.

The method may further comprise determining a pair of electrodes which is most closely aligned with a selected axis of the vessel.

The method may further comprise determining vessel collapsibility or deformity over at least one respiratory cycle.

The method may further comprise delivering a sinusoidal waveform and cycling through each electrode pair taking impedance measurements or capacitive measurements.

The method may further comprise performing an impedance to distance calibration based on initial resting dimensions of the electrodes, and performing a geometric reconstruction based on the assumption that the blood vessel has an elliptical shape.

The method may further comprise processing data from the electrodes on the basis of impedance planimetry.

The method may further comprise applying an alternating current, AC, across an outer pair of the plurality of electrodes.

The method may further comprise measuring AC voltage between an inner pair of the plurality of electrodes, the inner pair positioned between the outer pair of electrodes.

In accordance with the present invention there is further provided a blood vessel monitoring method comprising:
  implanting a plurality of implantable electromagnetic beacon transponders in a blood vessel, on, adjacent or in a blood vessel wall, the transponders adapted to emit a signal when excited;
  exciting the transponders; and
  receiving emitted signals and monitoring relative positions of the implanted transponders.

The method may further comprise detecting a resonant frequency of each transponder to differentiate the transponders.

The method may further comprise determining a cross sectional area of the vessel.

The method may further comprise determining the blood vessel diameter based on the relative positions of the implanted transponders.

We describe in various embodiments a blood vessel monitoring system comprising:
  a support structure configured to engage a vessel wall,
  a plurality of electrodes supported by the support structure,
  a drive circuit for delivering drive signals to the electrodes,
  a signal processing circuit for processing electrode parameters resulting from the drive signals to determine distance between the electrodes and estimate a vessel dimension,
  a communications circuit for communication with an external component.

Preferably, the signal processing circuit is configured to monitor impedance between electrodes as representative of vessel deformation.

Alternatively, the signal processing circuit is configured to determine capacitance between the electrodes, and the signal processing circuit is configured to monitor capacitance between electrodes as representative of a vessel dimension.

The support structure may be configured with a radial elasticity and compliance to have insignificant impact on the motion of the vessel wall. Alternatively, the support structure may be configured to alter normal physiologic motion of the vessel in a consistent and predictable manner and the signal processing circuitry is configured to apply a correction factor to the determination of vessel diameter or collapsibility.

In one aspect, the electrodes are arranged to engage a vessel wall at a first location and the support structure is arranged to engage a vessel wall at a second location, the first location being longitudinally separated from the second location by a distance selected such that natural movement of the vessel wall at the first location is not constrained by the support structure. Preferably, each electrode is coupled to the support structure by a connecting strut extending from an anchored part of the structure, the connecting strut being flexible or biodegradable and configured to bias the electrode into engagement with the vessel wall.

In other embodiments, the electrodes are mounted to a compliant support structure with sufficient elasticity to collapse and expand with the vessel without constraining the vessel's natural physiological shape changes. The support structure may be a stent-like flexible, elastic, cylindrical structure comprised of a slotted tube, interconnecting struts, or mesh, and/or having a continuous zig-zag or sinusoidal geometry. Notably, the support structure does not provide a scaffold to maintain lumenal patency as does a stent, but rather is designed to minimize any interference with the natural collapsing of the vessel in correlation with fluid volume. In some embodiments the support structure will alter natural vessel collapse or expansion by a known factor which can be accounted for by the processing circuit in determining vessel diameter or collapsibility.

Preferably, at least one connecting strut may be cantilevered from the anchored part of the structure.

Preferably, at least one strut may comprise an anchoring feature for engagement directly with a vessel wall, such as a barb or hook, or is configured to endothelialize on a vessel wall.

In one example, at least some of the electrodes may have an anti-fouling surface.

Preferably, the anti-fouling surface may include one or more selected from carbon nanotubes, conductive polymers, hydrogels, conductive hydrogels, bioactive coatings, and a tissue engineered neural interface.

Preferably, the system may comprise reference electrodes mounted to be a fixed distance apart, and the drive circuit and the signal processing circuit are configured to drive the reference electrodes and process resultant electrical parameters to monitor variations in the conductivity of the intervening media (blood, tissue etc.) and to apply a correction factor accordingly.

The reference electrodes may be mounted to be spaced apart in a longitudinal direction.

There may be a plurality of pairs of electrodes mounted circumferentially, and the circuits may be configured to estimate distances across different diagonals or chords.

Preferably, at least two electrodes are spaced apart in the longitudinal direction and the signal processing circuit is configured to drive and process data from the electrodes on the basis of impedance planimetry.

The electrodes may be mounted and the signal processing circuit is configured to determine cross-sectional area at a mid-point between said electrodes.

Preferably, the signal processing circuit is configured to estimate vessel diameter based on measured chordal distances.

Preferably, the signal processing circuit is configured to estimate a parameter value derived from distance, for example blood velocity and/or pressure gradient across a vessel. Preferably, the signal processing circuit is configured to provide real time measurements.

Preferably, the signal processing circuit is configured to execute an algorithm to reduce effects of fouling and/or endothelialisation on electrode surfaces.

Preferably, the algorithm includes one or more of the steps of performing impedance-to-distance calibration based on resting dimensions, salinity recalibration with scales impedance measurements with reference change; geometric reconstruction with elliptical assumption, fouling detection and rejection according to electrode geometry, preferably with data from three or more electrodes to reconstruct an ellipse, additional data used to detect and reject fouling.

Preferably, the signal processing circuit is configured to perform data correction with parallelogram edge and diagonal correction, by averaging opposed parallelogram sides.

Preferably, the signal processing circuit is configured to perform ellipse reconstruction to model a vessel shape, based on chordal lengths such as parallelogram side calculations. The circuits may be configured to apply a correction to compensate for change from a round to elliptical shape of the support structure in end view.

The circuits may be configured to allow selection of various pairs of electrodes to which drive signals are delivered. The signal processing circuit may be configured to compare a parameter between the various pairs of electrodes.

Preferably, the signal processing circuit is configured to determine a pair of electrodes which is most closely aligned with a selected axis of the vessel, preferably an anterior-posterior axis. The circuits may be configured to perform said processing by determining a major axis of an ellipse modelling shape of a blood vessel.

Preferably, the signal processing circuit is configured to determine vessel collapsibility or deformity over at least one respiratory cycle.

The support structure may be arranged with radiation-detectable markers and/or physical features to allow deployment with at least one pair of electrodes separated in an anterior-posterior dimension.

Preferably, the drive circuit is configured to deliver a sinusoidal waveform for at least one contact electrode pair and at least one capacitive electrode pair, and the drive and signal processing circuit is configured to cycle through each electrode pair taking impedance measurements and capacitive measurements.

Preferably, the signal processing circuit is configured to perform an impedance to distance calibration based on initial resting dimensions of the electrodes, and to perform a geometric reconstruction based on the assumption that the blood vessel has an elliptical shape.

The electrodes may include at least two passive electromagnetic transponders, and the system may comprise external drive coils and a sensing array to monitor relative positions of the implanted transponders. Preferably, the sensor array is configured to detect a resonant frequency of each transponder to differentiate the transponders.

Preferably, there are greater than two transponders, and the data processor is configured to determine cross sectional area of the vessel.

In another aspect, the disclosure provides a non-transitory computer readable medium comprising software executable by a digital processor to perform operations of a signal processing circuit of a system of any embodiment.

BRIEF DESCRIPTION OF THE DRAWINGS

The disclosure will be more clearly understood from the following description of some embodiments thereof, given by way of example only with reference to the accompanying drawings in which:

FIGS. 12 to 16 are sets of diagrams and equations for data processing with computation and correction;

FIG. 20 is a diagram showing a further device also using low frequency magnetic techniques, in this case wired;

FIG. 21 is a pair of diagrams illustrating some operating parameters; and

DETAILED DISCLOSURE

In various embodiments blood vessel monitoring systems are described which include implantable devices with a number of electrodes, a data processing subsystem, a communications subsystem, and a battery power source. The implantable device has a stent-like support structure for both anchoring and positioning the device within a vessel such as the IVC, and supporting the electrodes and some internal electronics for driving the electrodes and routing data externally. The support structure is flexible and elastic, preferably having little influence on the normal movement and shape of the IVC. In most cases the implantable device is deployed in a manner similar to a stent, within a catheter, and it expands radially to engage the blood vessel upon withdrawal of a sheath.

Implantable Devices

Figure 1:
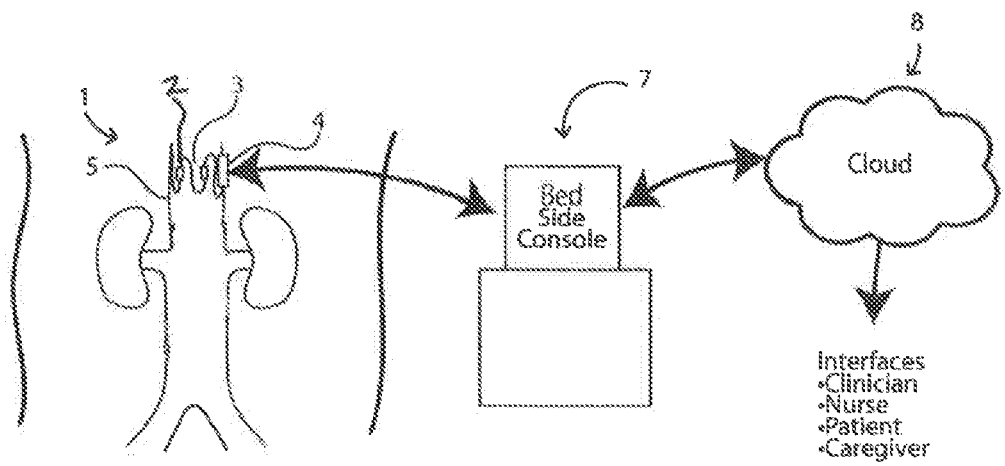
FIG. 1 is a schematic diagram showing a system of the disclosure incorporating an implantable device.
Figure 2:
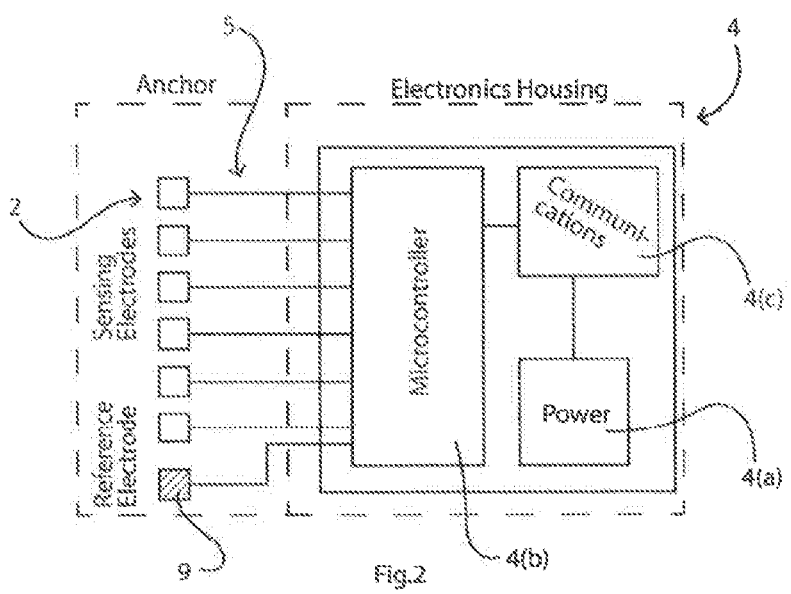
FIG. 2 is a block diagram showing a circuit of the implantable device.
Figure 3:
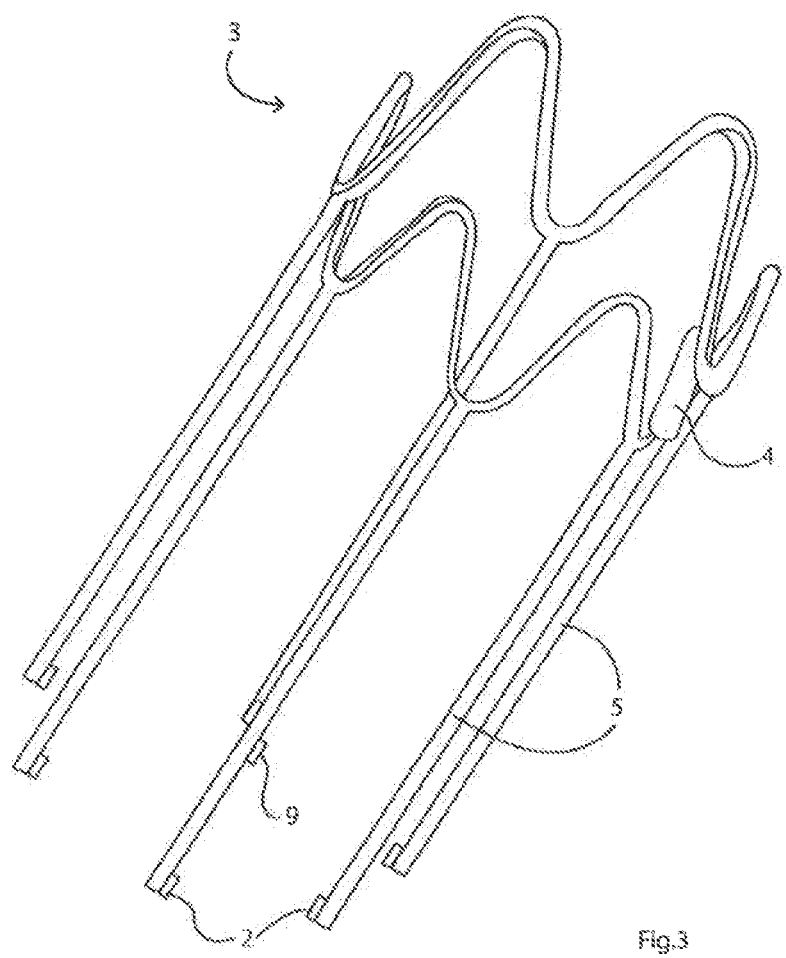
FIG. 3 is a perspective view of the implantable device.

Referring to FIGS. 1 to 3, a system of the disclosure is shown. The system comprises an implantable device 1 having sensing electrodes 2 coupled to a stent-like support or anchor structure 3. One of the struts 5 also has a reference electrode 9, for use in correcting for variations in blood conductivity. There are electrical connections to an electronic circuit in a housing 4, containing power 4(*a*), microcontroller 4(*b*) and communications 4(*c*) components as shown in FIG. 2, all mounted on the anchor structure 3. The implantable device 1 communicates wirelessly to an external console 7, which includes data processing circuitry as well as circuits for communication to cloud servers 8. Remote interfaces are provided for use by care providers, nurses, physicians, and the patient which can receive and/or transmit data from the external console 7 via a cloud server 8.

Referring especially to FIG. 3, in the implantable device 1 the multiple electrodes 2 and 9 are mounted on the cantilevered longitudinal struts 5 extending from the support structure 3. There are active and reference electrodes 2 and 9 mounted a short distance apart on one strut 5 in a manner whereby their separation is fixed. This allows calibration to detect changes in conductivity between the electrodes, so that impedance measurements between electrodes having a variable separation can be corrected.

Figure 4:
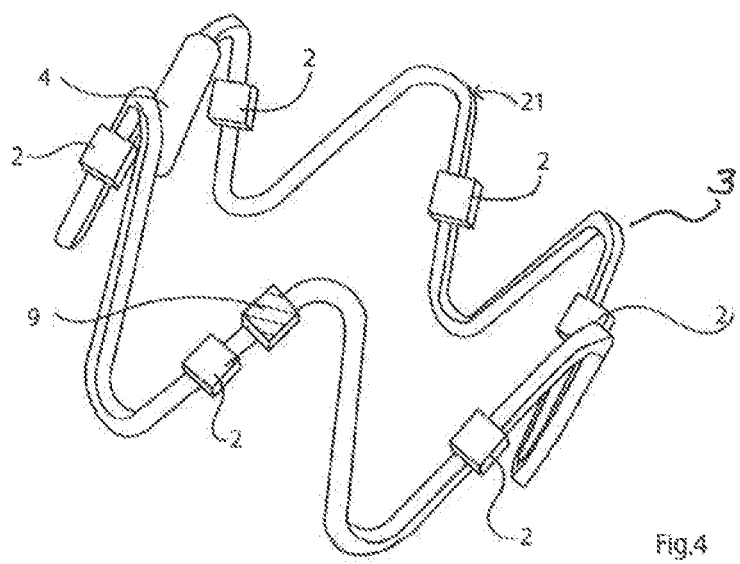
FIG. 4 is a perspective view of an alternative implantable device, without longitudinal struts.

However, in another embodiment shown in FIGS. 1 and 4 there may be electrodes 2 and 9 mounted directly on a structure 21. The anchor structure 21 has a sinusoidal wave-like pattern for radial expansion and collapse. In this case the structure 21 has a low radial force to avoid 'stenting' the vessel and preventing the vessel from moving (and thus negating the sensing). Where particularly low radial force is required, then additional means of anchoring are preferably incorporated to prevent the device from migrating, such as one or more of the following:

Anchor spikes such as sharp spikes to interact with the vessel wall.
Anchor features to anchor or hang the device from the renal vein or veins.
High friction surfaces to interact with the wall.
Ingrowth-promoting material, such as a polyester, to accelerate tissue ingrowth.
Oversizing—low radial force could be maintained while still setting the natural uncompressed diameter of the device to much greater than the maximum diameter of the vessel.

An implantable device may have an arrangement of electrodes mounted directly to the support structure 21 as shown in FIG. 4 in addition to electrodes mounted on longitudinal struts as shown in FIG. 3, the two sets being used at the same time or in an alternating manner for redundancy, calibration, comparison or averaging for higher accuracy, or other purposes.

Because the electrodes 2 of the implantable device 1 are insulated from or arranged outside of the support structure 3, any potential electrical interference from the structure and electronics is minimized, thereby allowing measurements to be taken in a portion of the vessel not affected by the support structure 3. Advantageously, there is physical separation of the electrodes from the support structure so that any distortion of vessel shape/collapsibility by the support does not influence the vessel shape where electrodes are located.

In various examples, the electrodes 2 are disposed at the tips of elongated flexible struts (numbering between two and eight) which are biased outwardly in a cantilevered manner into contact with the vessel wall and are sufficiently flexible to allow the electrodes 2 to move inwardly and outwardly with the natural collapse and expansion of the vessel. The struts preferably have a length selected such that the electrodes 2 are positioned far enough from the support structure 3 that in the region engaged by the electrodes 2 the vessel undergoes its natural collapse and expansion without being constrained or distorted by the support structure 3, which is preferably at least about 30 mm in length.

The support structure 3 is preferably stent-like and may take any suitable stent or anchor type form, as is well known in the art, providing support for the electrodes in a secure manner within the blood vessel. The support structure properties may be of the type known for supporting IVC filters for example. The structure 3 supports the electronics unit 4 containing the circuit which provides electrode drive signals, and performs signal processing from them and wireless delivery of data to the external console 7. If the support does influence vessel shape, it preferably has a known and predictable amount that can be characterised empirically in testing and corrected for in the calculation of vessel diameter, and the system is preferably programmed to compensate for it. The stent may be either super flexible/compliant so that it does not influence vessel shape significantly, or the amount of distortion should be predictable and included in the calculation.

Some or all electrodes may be mounted to the inside of the support structure (closer to the centre of the lumen) in which case the thickness of the support structure would be corrected for. Alternatively, at least some may be mounted to lie alongside the members, at the same radial position. In a further example, at least some may be radially outside the members and hence in contact with the vessel wall in use.

The support structure may have one, two, or more rings or hoops and interconnecting longitudinal members.

Each longitudinal strut 5 has a Nitinol spine, coupled to which are insulated leads for the electrodes 2.

In some embodiments, the electrodes 2 and/or the longitudinal strut 5 may be configured to be fixed to the vessel wall to ensure that the electrode moves with it. For example, the electrode 2 and/or the longitudinal strut 5 may have barbs, hooks, or other features on its outer side that penetrate or engage the wall tissue. The electrode 2 and/or longitudinal strut 5 may alternatively or additionally be coated with a material that adheres to tissue or encourages tissue growth around or into these components. In other embodiments the longitudinal strut 5 may have a tip extending beyond the electrode 2 and configured to penetrate into the vessel wall.

The structure 3 diameter is preferably in the range of 5 mm to 40 mm, and the length is preferably in the range of 10 mm to 40 mm.

In various embodiments, the support structure 2 may have one, two, or more rings or hoops and interconnecting longitudinal members or struts between the hoops, the hoops being resiliently biased radially outwardly in a stent-like manner to engage the vessel wall and securely anchor the device 1 in the vessel. The rings or hoops may have a sinusoidal, zig-zag, or other radially collapsible configuration to facilitate delivery through the vessel to the desired location of placement and to impart a relatively consistent radial fixation force against the vessel wall over a wide range of diameters.

The support structure may also have other anchoring features such as those which are known for IVC filters and commonly known in the art.

The microcontroller, measurement circuitry, the communication sub-system, and the battery are located within the electronics enclosure 4, which is hermetically sealed. An alternating current is sequentially applied between pairs of electrodes 2 and the measurement circuitry determines an impedance measurement between at least two of the electrodes 2. If it is assumed that the blood conductivity is constant, the impedance measurement between the active electrodes is related to distance between them. It is therefore possible to obtain information on the relative distances between electrodes, allowing IVC diameter and possibly also other data such as cross-sectional area and shape to be determined. The inclusion of a reference electrode 9 enables the system to accommodate changes in the conductance of blood as the reference electrode 9 is at a known distance from a sensing electrode 2 and internal calibration is performed automatically. The reference electrode 9 also facilitates some calculations to reject or correct for any changes with endothelialisation and the resulting changes in conductance.

Measurement of IVC diameter or collapsibility has certain unique considerations and challenges not present in the measurement of other blood vessels. One such challenge is the asymmetrical shape and dynamics of the vessel as it collapses and expands. The IVC tends to collapse in the anterior-posterior direction, moving from a more circular cross-section at higher blood volumes to a flattened, oval cross-section at lower blood volumes. Thus the direction of measurement is an important factor. The device 1 may be specially configured to enable the determination of the vessel dimensions and/or collapsibility in a desired direction (e.g. anterior-posterior). For example, the support structure 3 may have radiopaque or ultrasonic markers to guide the user during placement so that it may be oriented with electrodes 2 along the desired axis. Alternatively, the support structure 3 may be configured to self-orient by means of varying circumferential radial force, into a desired rotational position in the IVC upon deployment such that a pair of the electrodes 2 are disposed along the anterior-posterior axis.

In various embodiments, the implantable device has a circumferential array of electrodes disposed at a predetermined circumferential spacing from each other as shown in FIGS. 3 and 4. For example, three, four, five, six or more electrodes may be arranged around the circumference of the device 1. The system may be configured to allow selection of various pairs of electrodes between which impedance or other parameters may be measured. The maximum and minimum distances between various electrode pairs may thus be determined so that the pair most closely aligned with the anterior-posterior axis may be selected. Such selection may be performed manually by the user, or the system may be configured to automatically sample various electrode pairs and determine through software which pair is oriented closest to the desired axis of measurement, and/or between which pair the diameter variation or collapsibility is greatest or lowest. This embodiment could also be utilized to estimate irregular shapes of IVC cross section which may be useful in understanding particular blood volume patient states.

Sensing and Blood Conductivity Correction

Figure 5:
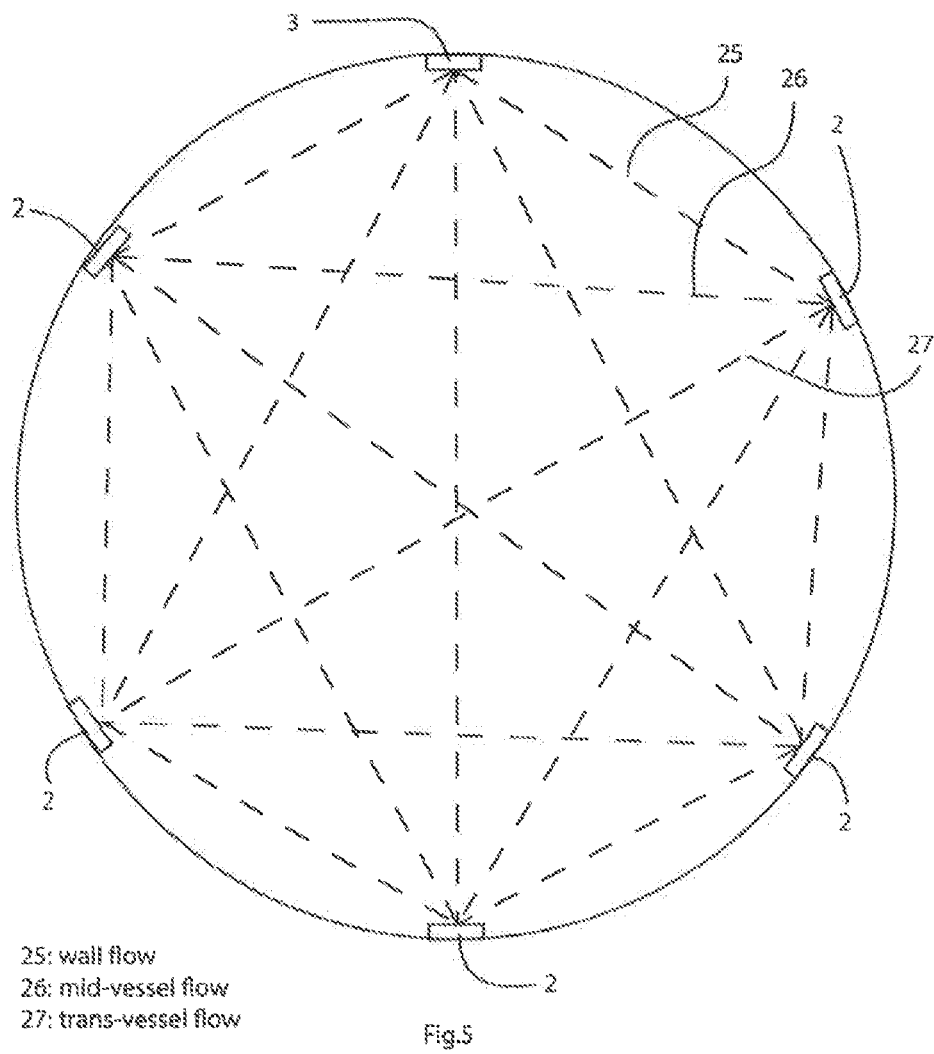
FIG. 5 is a diagrammatic end view showing how the electrodes are arranged circumferentially and how they can be driven and signals processed for different permutations of pairs.

The presence of multiple electrodes facilitates numerous pairs to be selected and impedance measurements taken and subsequently converted into distances and then derived parameter values. As can be seen in FIG. 5, with six electrodes 2, there are multiple ways to calculate the position of any one electrode. All or a portion of the distances between an electrode and each other electrode on the implant may be calculated. This over-constrained problem provides redundancy in the system and allows for errors or drift to be corrected for in the algorithms.

However, blood conductivity is reliant on a number of blood properties which may vary over the course of the day/year:

Glucose may vary over the day by 50-100%. It has a direct effect on conductivity, different ranges for normal/diabetes patients.

Orientation of Erythrocyte cells affects conductivity and dielectric properties.

Environmental factors, such as exposure to pollutants (e.g. Benzene), can cause 40% variation.

Blood Type: Dielectric properties can vary by up to 50% depending on A, B, AB and O Blood type.

Haematocrit may vary annually by approximately 15% due to blood loss.

Support structure material may also affect electrical conductivity.

Given blood conductivity variability, it is preferred that the measurements have an empirical correction factor accounting for blood conductivity. This is achieved by use of the reference electrodes 9 within the structure or on a linked structure which maintains them at a fixed separation from an adjacent sensing electrode 2.

The correction factor is preferably obtained by fixing two electrodes a set distance apart, measuring blood impedance and using this as a correction. Such reference electrodes are preferably spaced-apart in the longitudinal direction because it is simpler to maintain a fixed separation in this direction. However, they may alternatively be radially spaced-apart.

The IVC contracts and expands with each respiration (and to a lesser extent with each heart beat). Regular IVC diameter measurements are thus taken over multiple respiratory cycles allowing for the recording of maximum and minimum diameters, with which a measure of collapsibility can be determined.

The recorded data may be stored in a memory device within electronics enclosure 4, and transmitted via Radio Frequency (RF) communication to the external console for processing and display. Alternatively raw measured signals may be transmitted upon measurement directly to the external console where they are stored and processed.

Impedance Planimetry Approach

Figure 6:
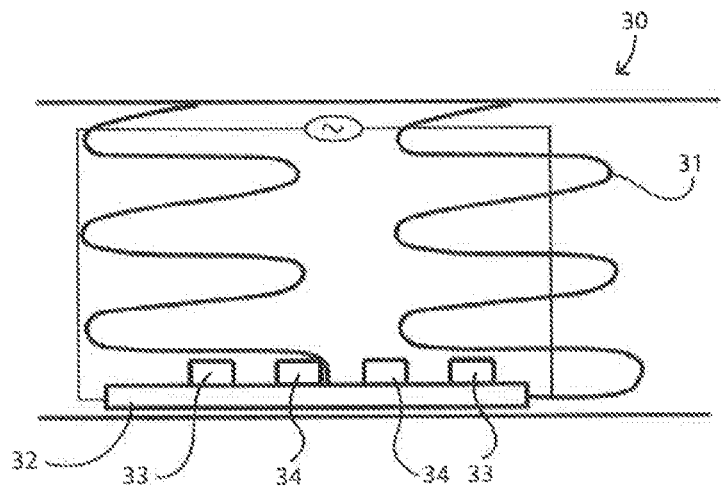
FIG. 6 is a diagrammatic side view of an alternative device, in which the sensing electrodes are distributed longitudinally along the vessel wall, for impedance planimetry measurements.

In other embodiments, at least some of electrodes 2 are arranged longitudinally and in-line, at fixed distances apart. FIG. 6 shows a device 30 having a stent-like support 31, a substrate 32, power electrodes 33, and sensor electrodes 34. The IVC cross-sectional area measurement technique is based on impedance planimetry. An alternating current (AC) is applied across the outer powered pair of electrodes 33 while AC voltage measurements are made between the inner pair of sensor electrodes 34 positioned mid-way between the powered electrodes. The AC voltage measurement is inversely related to the cross-sectional area of the IVC, assuming a constant AC power source and a medium of constant conductivity.

This embodiment is advantageous because it uses impedance planimetry without the use of a balloon filled with media within which to set up the electric field. In the present disclosure, the existing blood flow within the vessel is used to do this. A constant current source is applied at the power electrodes shown and the sensing is done between them using the sensor electrodes shown. An advantage of this system is that it gives an actual area of the lumen (irrespective of shape), it could also be deployed over a larger/longer area, and it may require less processing power and post processing.

The AC voltage measurements allow estimation of the extent of the diameter of the vessel at the mid-point between the power electrodes 33. It is important that the voltage drop across the medium is generated from a constant AC current source. The fact that the conductivity of the blood is not constant may give rise for a need to apply a correction factor (and potentially using the electrode array as a set of reference electrodes) as described above.

Switching Array

Figure 7:
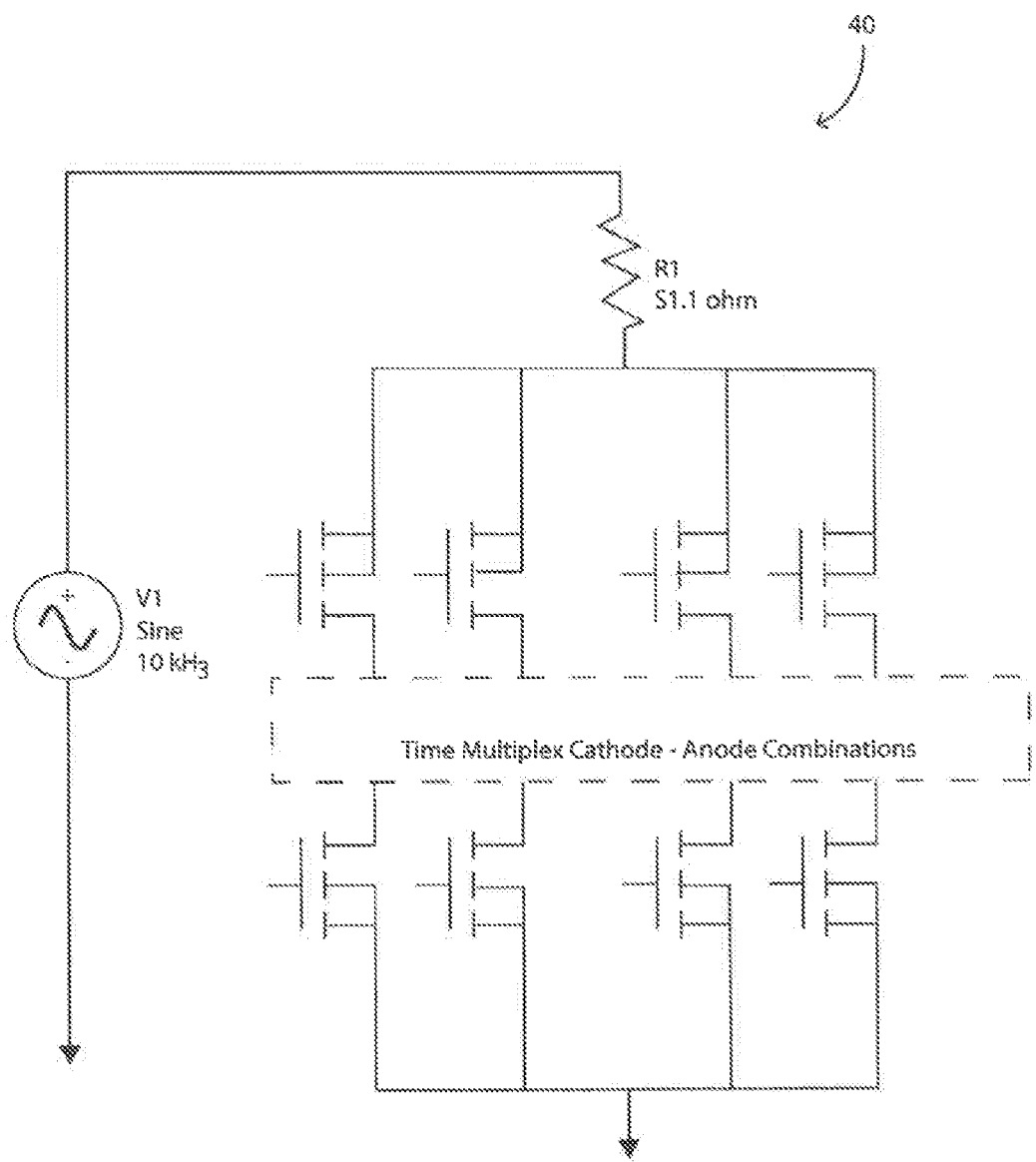
FIG. 7 is a circuit diagram of a switching array for the sensing electrodes of the devices of any embodiment.

FIG. 7 shows a switching array 40 for driving electrodes of any embodiment. In the switching array 40 the switching controller runs through the combinations of source detector pairs by using a series of programmable solid state switches to create an electrical path between the source and an electrode and also creating an electrical path from the opposite paired electrode current detection path to ground to close the circuit.

The switching array 40 is connected to impedance measurement circuitry, which preferably includes an impedance analyser chip, and a SoC (System on chip) for the main data processing within the electronics enclosure 4, and from there data is communicated wirelessly to the external console.

In exemplary embodiments the microcontroller 4(*b*) (FIG. 2) delivers a 100 kHz sinusoidal waveform that consumes 2 mW for the contact electrodes, and 2 μW for capacitive electrodes. The algorithm cycles through each electrode 2 pair taking impedance measurements.

The drive frequency is preferably at least 100 kHz.

Data Processing

In executing an algorithm to determine collapsibility the following factors and considerations are applied by the data processor:
- expected respiration and cardiac cycle periods;
- expected maximum and minimum IVC diameters;
- corrections for blood conductivity and conductivity changes due to gradual endothelialisation using reference electrode measurements;
- any calibrations that may be required at implantation; and
- corrections facilitated due to the over constrained nature of the solution set and multiple measurements for each dimension.

The recorded data is stored and transmitted via Radio Frequency (RF) communication to the external console 7. Some data processing may be done with a processor or processing circuitry in the implant prior to transmission externally. Optionally the data may be stored in a memory device on the implant. Alternatively, only raw electrode signals correlated with measured electric parameters such as impedance or capacitance are transmitted wirelessly, and the required data processing is performed by processing circuitry in the console 7, which may be a computer, or a smartphone, or any other computing device.

It will be understood that in any of the embodiments described herein, the terms "signal processing circuit", "processing circuitry," and the like may refer to circuitry and/or processors within the electronics housing 4 on the implant, in the external console 7, or combinations thereof, and the data processing and calculations performed by the processing circuitry may be performed entirely within the implant, entirely in the external console, or partially in each. Further, in some embodiments, the external console may communicate with remote computer systems via Bluetooth, wireless or wired communication, and some or all of the data processing referred to herein may be performed on such remote systems.

The impedance to distance calibration is based on the initial resting dimensions of the electrodes. If the impedance of the blood changes with respect to time, all of the impedance measurements are scaled with respect to the reference electrode set. A geometric reconstruction may be performed based on the assumption that the IVC has an elliptical shape. Fouling detection and compensation may be performed with either of two methods, geometric or time-dependent, as described more fully below.

Figure 8:
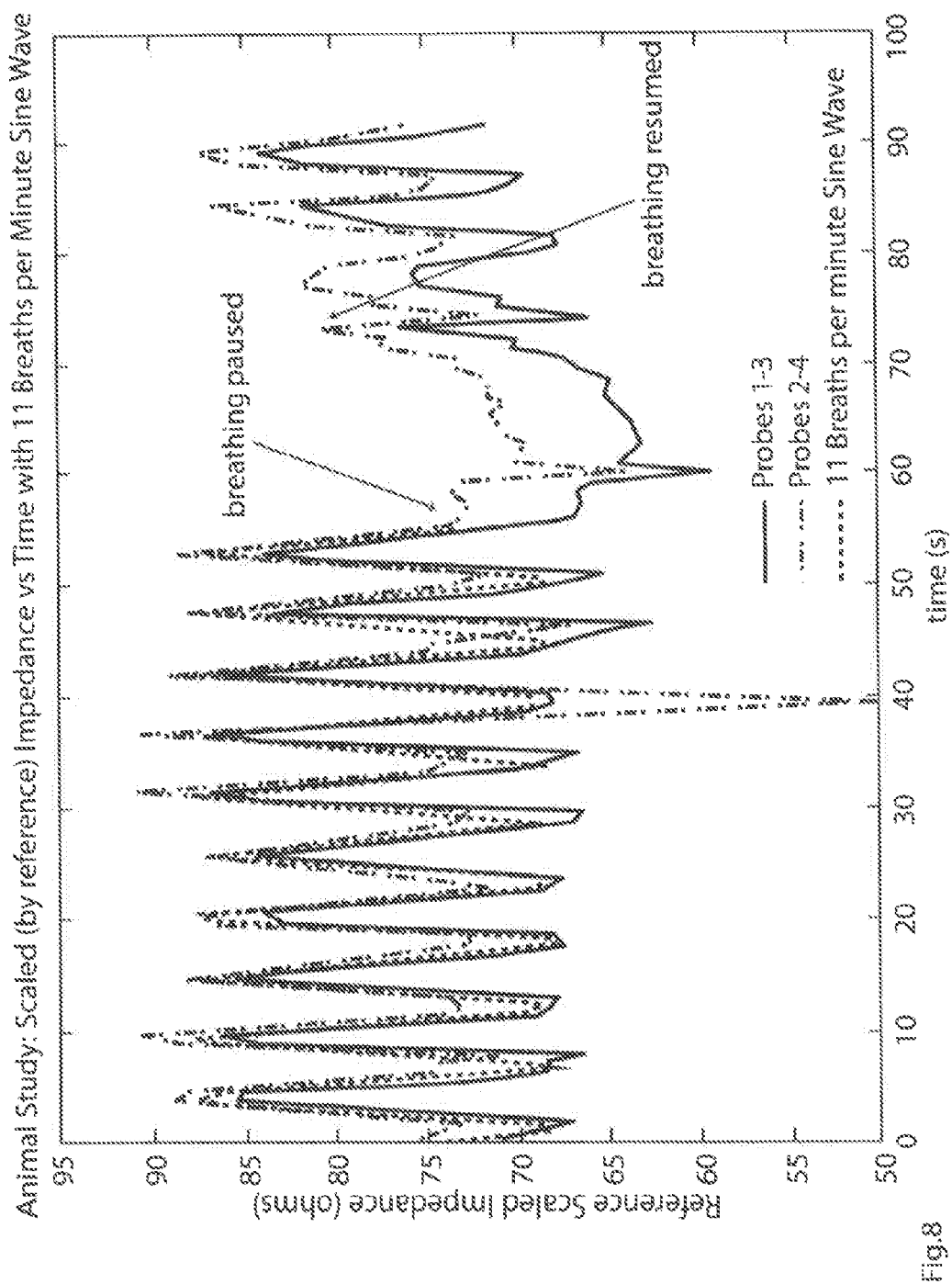
FIG. 8 is a plot of impedance vs. time for a test using the device of FIGS. 1 to 3.

FIG. 8 is a plot of impedance vs. time for an animal study using the device shown in FIG. 4, showing the impedance between the pairs of electrodes 2 varying in synchronism with the IVC distension. It may be seen that the impedance between pairs of electrodes varies as the wall of the IVC moves. The frequency of the variation in the wall of the IVC and therefore the signal, is determined by the rate set on the mechanical ventilator (11 breaths per minute in this case). When the ventilator is stopped (simulating breath hold) the variation in the impedance stops and recommences when respiration is restarted, again demonstrating that the signal seen is a direct result of the IVC wall motion induced by the ventilator.

Figure 9:
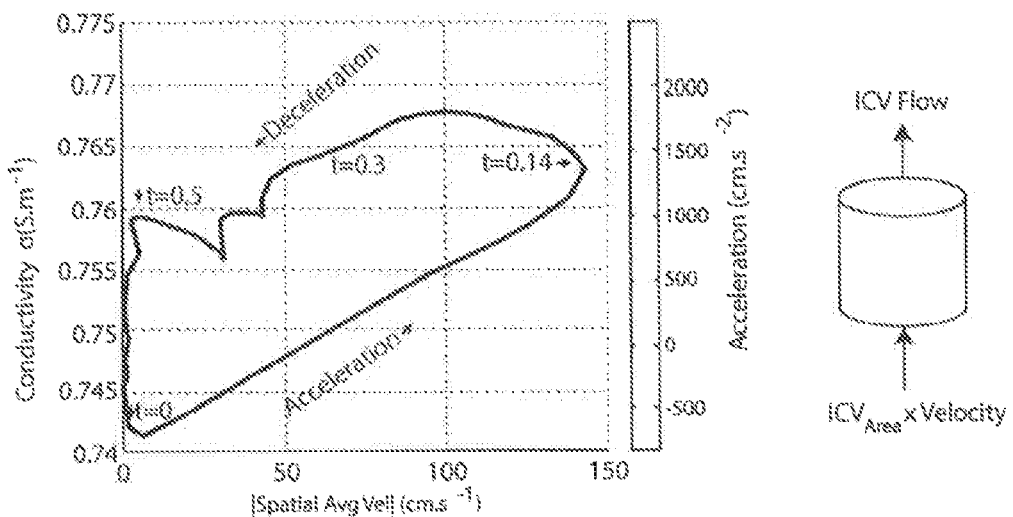
FIG. 9 is a plot of the conductivity of blood as it changes with velocity.

In diagnosing and monitoring heart failure, it may be valuable to determine other parameters such as blood flow velocity and/or pressure gradient, or $\Delta P/\Delta x$. FIG. 9 shows the relationship of blood conductivity as a function of flow velocity. It may be seen that conductivity increases with flow velocity. This relationship presents the opportunity to determine blood flow velocity based upon the determination of impedance between electrodes. From blood flow velocity and vessel radius, pressure gradient may be calculated.

Figure 10:
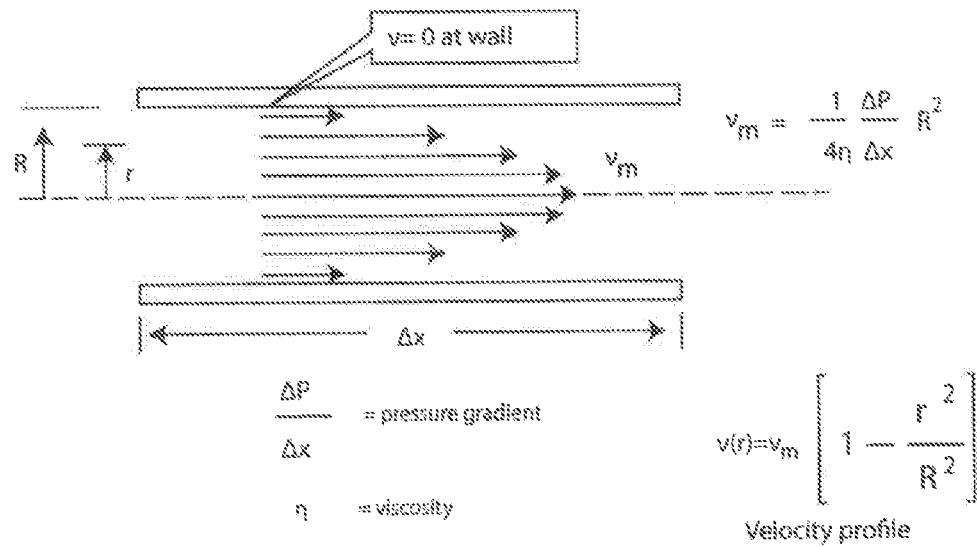
FIG. 10 is a diagram showing the velocity profile across the vessel.

FIG. 10 shows several of the key parameters for the data processing performed by the system when calculating the blood flow from the individual velocities inferred between pairs of electrodes. It will be seen that the radius "R" at any point in time is a parameter in calculation of the velocity for any radial position "r", which in turn is related to the pressure gradient $\Delta P/\Delta x$. In more detail:

$$v_m = \frac{1}{4_n} \frac{\Delta P}{\Delta x} R^2 \text{ where } \frac{\Delta P}{\Delta x} = \text{pressure gradient,}$$

and $n$ = viscosity and, $$v(r) = v_m \left[1 - \frac{r^2}{R^2}\right]$$

gives the velocity profile.

This information may be used in combination to compute the blood flow rate. Vessel diameter may be determined using the impedance and, using different chords as shown in FIG. 5 through the cross section and the variation of conductance with velocity, each chord could be assigned a velocity. These velocity profiles could then be combined to compute a blood flow rate, or pressure gradient, or flow velocity.

The switching array sequentially connects each pair of electrodes to the impedance analyser chip within the electronics enclosure 4, which determines the impedance measurement for that pair of electrodes. Each of these results is then recorded on the SoC (which is part of the communications block 4(*c*)) which also performs the communications function to transmit the stream of data to the external console 7.

One approach for this device is to allow the electrodes to endothelialize and therefore reduce the risk of thrombus or embolization. This does however bring the challenge of managing the potential changes in impedance due to the varying media and tissue thickness between the electrodes. A reference electrode may be utilized as a solution to this issue as described above. An alternative option is to prevent the electrodes from being incorporated into the vessel wall. In this situation the electrodes are exposed to blood and may be subject to fouling due to thrombus formation. Antifouling coatings may be used for the implanted electrode surfaces. The coatings may comprise one or some of carbon nanotubes, conductive polymers, hydrogels, conductive hydrogels, bioactive coatings, and a tissue engineered neural interface.

One or more of the following approaches may be used to compensate or correct for the effects of fouling.

Figure 11:
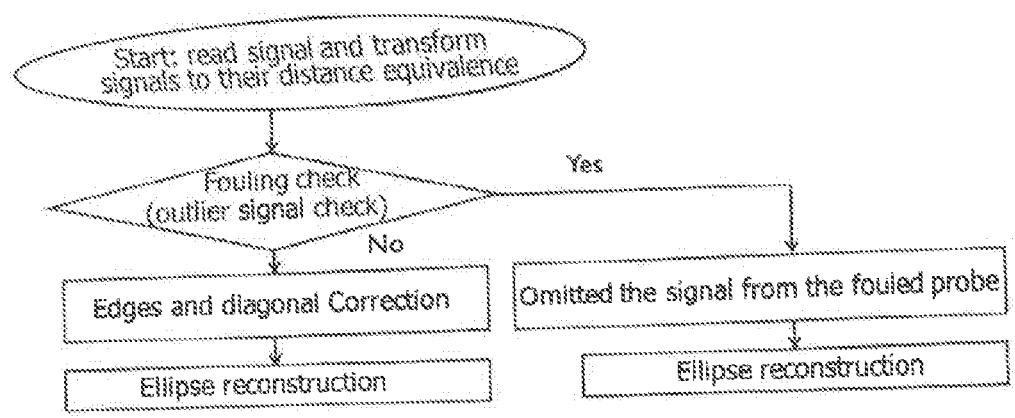
FIG. 11 is a flow diagram showing operation of a signal processor for processing data from the sensing electrodes.

- Impedance to distance calibration based on resting dimensions
- Salinity recalibration—scales impedance measurements with reference change
- Geometric reconstruction with elliptical assumption
- Fouling detection and rejection
  - Geometric
    - Requires data from 3 electrodes to reconstruct ellipse, and compensation data used to detect and reject fouling
  - Time-Dependent
    - Uses varying time scales to detect fouling FIG. 11 is a flow diagram for the overall data processing. Initially, the current signals are read from between each successive pair of electrodes in a drive scheme set by the microcontroller and the switching array. As shown in FIG. 5 there may be trans-vessel flow chords 27, mid-vessel flow chords 26, and/or wall flow chords 25. As a known voltage is applied between the electrodes of each pair and the current is detected, the resistance and hence distance can be determined by comparing the reference impedance to the impedances calculated from each electrode pair adjusted for any fouling correction.

The system processes derived data to recognize the asymmetrical shape change in the IVC, specifically the use of multiple electrodes to get dimensional measurement in multiple axes and reconstructs an ellipse from these dimensions.

There are preferably a sufficient number of electrodes to minimize the error of being oriented off-axis (i.e. not aligned with anterior-posterior axis of the vessel). There is preferably a minimum of four electrodes, but preferably at least six, arranged circumferentially around the implant, and the sampling is preferably of all possible electrode combinations in order to model the ellipse. The fouling detection and correction in software is very advantageous, and eliminates outliers in the detected data.

Also, advantageously in some embodiments the data processor is programmed to determine flow rate and/or pressure gradient in addition to vessel dimension, as described above.

The length of the structure helps it to conform to IVC or other blood vessel, and this is preferably in the range of 10 mm to 50 mm. For optimum performance, there is preferably one structure peak per electrode.

The processor is programmed to sweep through frequencies for fouling elimination/correction, as fouling will be detected more for some frequencies than others.

In the next step there is a fouling check, in which any outliers are eliminated. There is then edge and diagonal correction, followed by ellipse reconstruction.

FIG. 12 shows the construction of a parallelogram from chordal lengths $l_{12}$, $l_{34}$, $l_{14}$, and $l_{23}$ as determined by the impedance between two pairs of electrodes. A correction is then applied to both parallelogram edges and diagonals, in which opposed lengths are added and the sum divided by two. The parallelogram edge correction is thus based on the fact that the opposing parallelogram edges are equal to each other. Basic geometrical expressions as illustrated are used to determine the diagonals of the parallelogram. The subsequent diagonal correction is based on the minimal correction needed such that the intrinsic geometric relationship between parallelogram edges and diagonals can be satisfied.

Figure 13:
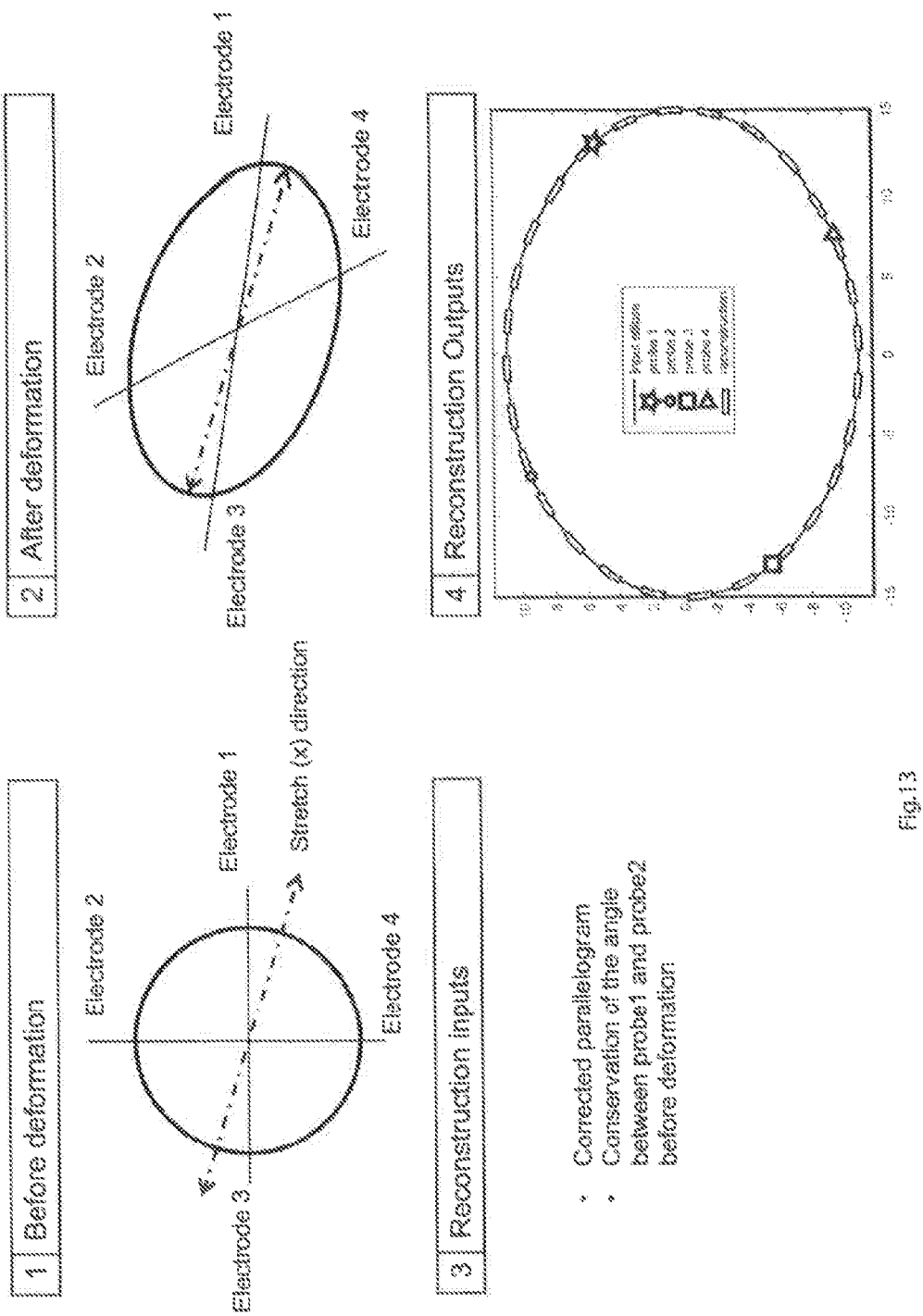

FIG. 13 shows ellipse reconstruction from the parallelogram, in which there is correction applied to compensate for change from a round (top left diagram) to elliptical (top right) shape of the support structure in end view. Two criteria for reconstructing the ellipse are:

- The reconstructed ellipse must encompass the parallelogram (the ellipse outline needs to pass through the four corners of the parallelogram). There is a stretch in an "X" direction, the longer diagonal or major axis of the parallelogram.
- When the reconstructed ellipse is transformed to its un-deformed circular shape, the diagonals of the corresponding parallelogram need to form an angle of 90°.

With the two criteria above, the reconstructed ellipse is uniquely defined.

The ellipse reconstruction algorithm is as follows, in which:

a and b are the parallelogram long and short side lengths, and c and d are the major and minor axes;

the electrodes are referred to as electrodes 1, electrode 2, electrode 3, and electrode 4 in sequence circumferentially around the vessel.

Define the included angle of the diagonals as:

$$\Phi = \frac{\mathrm{acos}(d^2 + c^2 - 4a^2)}{2dc}$$

Define the point 1 position and point 2 position as $$\begin{bmatrix} x_1 \\ y_1 \end{bmatrix} = \begin{bmatrix} \frac{c}{2} \\ 0 \end{bmatrix}, \begin{bmatrix} x_2 \\ y_2 \end{bmatrix} = \begin{bmatrix} \frac{d}{2}\cos(\Phi) \\ \frac{d}{2}\sin(\Phi) \end{bmatrix},$$

respectively.

Define an unknown θ to be solved later.

Two virtual positions which used to help reconstruct the ellipse are:

$$\begin{bmatrix} x_1' \\ y_1' \end{bmatrix} = \begin{bmatrix} \cos(\theta) & \sin(\theta) \\ -\sin(\theta) & \cos(\theta) \end{bmatrix} \begin{bmatrix} x_1 \\ y_1 \end{bmatrix}$$

$$\begin{bmatrix} x_2' \\ y_2' \end{bmatrix} = \begin{bmatrix} \cos(\theta) & \sin(\theta) \\ -\sin(\theta) & \cos(\theta) \end{bmatrix} \begin{bmatrix} x_2 \\ y_2 \end{bmatrix}$$

Based on the position relationship of electrode 1 and electrode 2 at unreformed position, the following relationship needs to be satisfied:

$$x_1'y_1' + x_2'y_2' = 0$$

θ can be solved by the equation above.

The corresponding major and minor axis of the ellipse are solved by $$\text{Major axis} = \max(\sqrt{x_1'^2 + x_2'^2}, \sqrt{y_1'^2 + y_2'^2})$$

$$\text{Minor axis} = \min(\sqrt{x_1'^2 + x_2'^2}, \sqrt{y_1'^2 + y_2'^2})$$

FIG. 14 shows the effects of noise and fouling on the ellipse.

Figure 15:
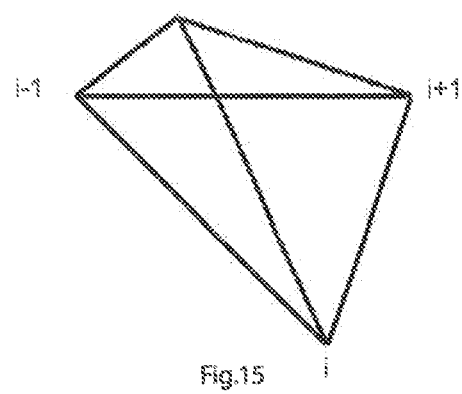
Figure 16:
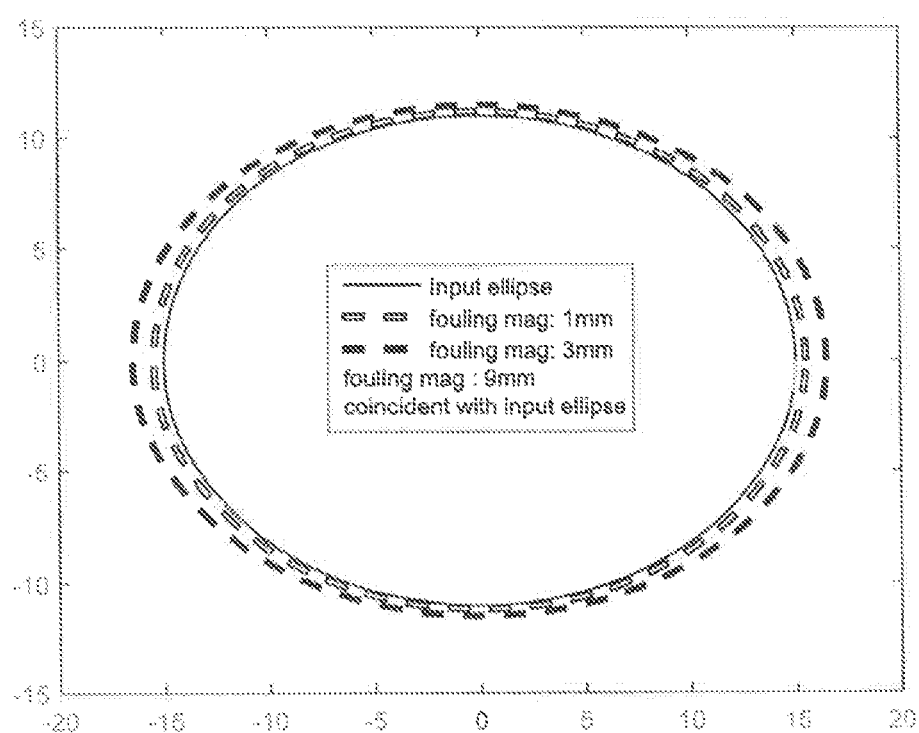

Referring to FIGS. 15 and 16, if the two edges associated with Electrode i ($l_{i,i-1}$ and $l_{i,i+1}$) are significantly larger than their corresponding opposite edges, the processor assumes that there is fouling on electrode. This may be corrected using the parallelogram edge and diagonal correction procedure described with reference to FIG. 12.

Figure 17:
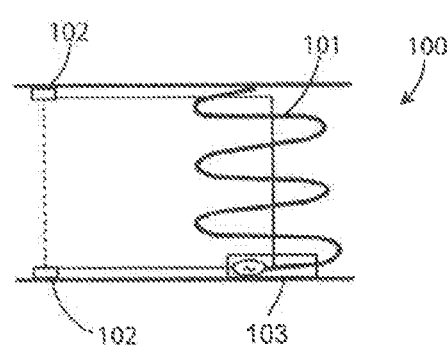
FIG. 17 is a diagrammatic side view of a device having capacitance sensing.

FIG. 17 shows a further embodiment in which the implantable device 100 has capacitance electrodes or pads. The device 100 consists of conductor pads (electrodes 102), a data processing subsystem, a communications subsystem, and a battery power source contained in a housing 103. The components are housed and incorporated into a stent-like support structure 101 for both anchoring and positioning the device within the IVC, in a manner as described above in any embodiment. The support structure is flexible and elastic, having little influence on the normal movement and shape of the IVC.

The electrodes are positioned such that they lie on the endothelium of the IVC wall on directly opposing interior wall. The electrode is arranged such that it extends outside of the stent support, thus minimising any electrical interference from the structure.

The drive circuitry may apply an alternating voltage across the two conductive electrodes, thus creating an effective capacitor with the blood as a dielectric material. The measurement circuit, e.g. an analyser chip, can then measure the capacitance between the electrodes. If it is assumed that the blood dielectric value is constant, the distance (corresponding to the IVC diameter) between the plates can be estimated accurately by measuring the capacitance. It is expected that the use of a capacitance measure may be less influenced by any intervening material (endothelial/blood/other cells).

Some or all of the features described above for the embodiments with sensing electrodes to measure impedance apply to this embodiment with capacitive electrodes.

Electromagnetic Aspect

In other embodiments, power may be provided to sensing electrodes by electromagnetism, and relative movement of beacon transponders may be tracked.

In these embodiments blood vessel monitoring systems include an implantable device with at least one electrode in the form of an electromagnetic beacon transponder, a data processing subsystem, a communications subsystem, and a battery power source. The electrodes are supported by a stent-like support structure for both anchoring and positioning the device within a vessel such as the IVC. The support structure is flexible and elastic, having little influence on the normal movement and shape of the IVC. Some or all of the features described above for the other embodiments may apply for the embodiments with beacon transponders, the transponders being mounted in a manner akin to the mounting of the sensing electrodes of any embodiment.

Figure 18:
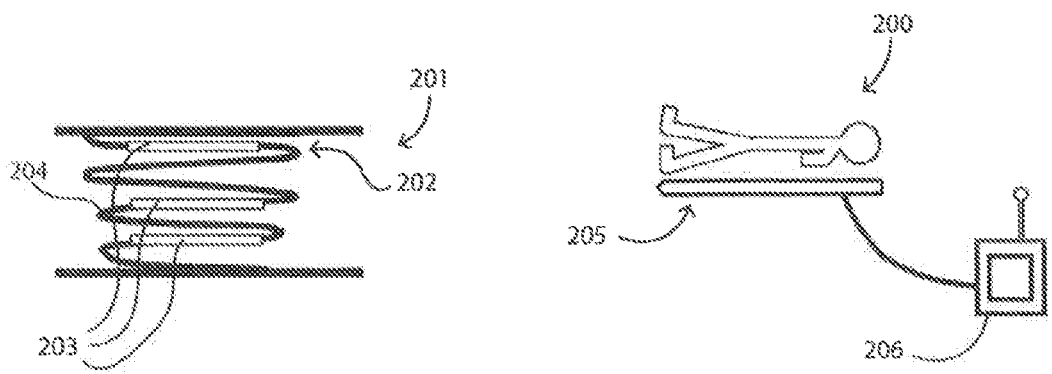
FIG. 18 is a diagram illustrating an alternative system of the disclosure for monitoring IVC diameter and collapsibility, in this case involving electromagnetic devices.

Referring to FIG. 18 a system 200 is described for providing measurement of IVC lumen diameter and collapsibility. An implantable device 201 comprises a stent-like support structure 202 with peaks 204, and a number of passive beacon transponders arranged 203 around the structure's periphery. There is an external electromagnetic coil and sensor array 205 linked with a data processing console 206. There is a communications subsystem and power source within one of the transponders 203, or alternatively in a separate hermetically sealed capsule mounted to the support structure.

The electromagnetic beacon transponder electrodes 203 are coupled to the stent-like support structure 202 such that they are positioned along the circumference of the IVC endothelium.

Each transponder 203 consists of a miniature electrical circuit contained in a sealed glass capsule, measuring approximately 1.85 mm in diameter and 8.0 mm in length. The transponders are preferably passive having no power source and, thus, are excited externally by the flat panel array 205 on which the patient lies. The flat panel 205 houses both a series of electromagnetic source coils and a sensor array. The transponders 203 are excited via the electromagnetic source coils of the array 205 with each transponder emitting a unique resonant frequency signal. The spatial profile of each resonant signal is detected by the multiple channel sensors, allowing for the position of each transponder to be determined.

Accordingly, the diameter of the IVC may be determined as the distance between opposing transponders 3, the spatial resolution of which is less than 0.25 mm. Alternatively, where multiple beacons are incorporated into the stent support structure 202, it may be possible to infer IVC cross-sectional area.

The data processing functions described above may be applied in any desired combination to this embodiment.

Figure 19:
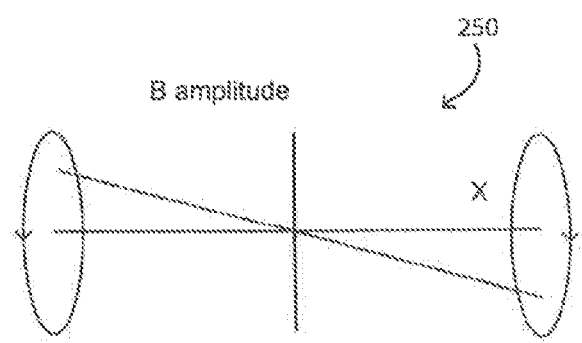
FIG. 19 is a diagram showing operating principle of the FIG. 18 system, using low frequency magnetic techniques, in this case wireless.

Referring to FIG. 19, coils 250 are within the beacon transponders 203 and the magnetic field between them is monitored at the "B amplitude" location. This is in response to a low frequency stimulus. There may be more than two coils, giving multiple axes for 3 dimensional (3D) positions. In this case the communication is wireless to a host which performs the data processing. The coils may have a 19 kHz resonant frequency, and the external stimulating array may have 32 coils to reconstruct position Referring to FIG. 20, in another embodiment an implanted device 300 has coils 301 and a sensing coil 303 is connected by a wired link 305 with an amplifier connected to signal processing circuits. In this case it is expected that a stronger external magnetic field may be applied.

Referring to FIG. 20, in another embodiment an implanted device configuration 300 has a pair of coils 301 used for excitation (transmission) and an implanted sensing coil 303. The sensing coil 303 is connected by a wired link 305 to the outside circuit with an amplifier connected to the signal processing circuits. The excitation magnetic field generated by the excitation coils 301 is assumed to vary linearly across the range of possible sensing coil locations and, in order to induce a measureable voltage in the sensing coil, the excitation current in the coils 301 is varied using a known resonance frequency (e.g. 19 kHz). The variation of the excitation magnetic field across space causes spatially-dependent magnitude shifts in the sensing coil 303 and hence the location of the sensing coil 303 within the body can be resolved. Pre-amplification is used to improve the signal-to-noise-ratio of the sensed signal in the sensing coil 303 and in order to reduce the necessary magnetic field strength to be created by the excitation coils 301. The same may be achieved through use of multiple array detectors.

Referring to FIG. 21, in an implantable device 350 transponders 351 are mounted around the periphery of an implantable support structure 352. There is an externally-applied magnetic field, operating at a frequency in the range of 100 MHz to 300 MHz. In one example, a 1 mm difference in separation of two opposing electrodes 351 gives a phase shift of 0.36°. The electrodes 352 are in this case passive, being powered by the external RF field.

Figure 22:
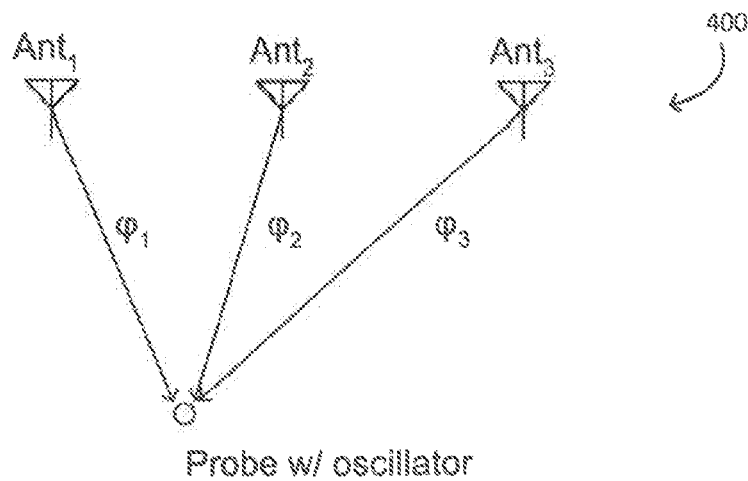
FIG. 22 is a diagram showing antennas for RFID type sensing.
Figure 23:
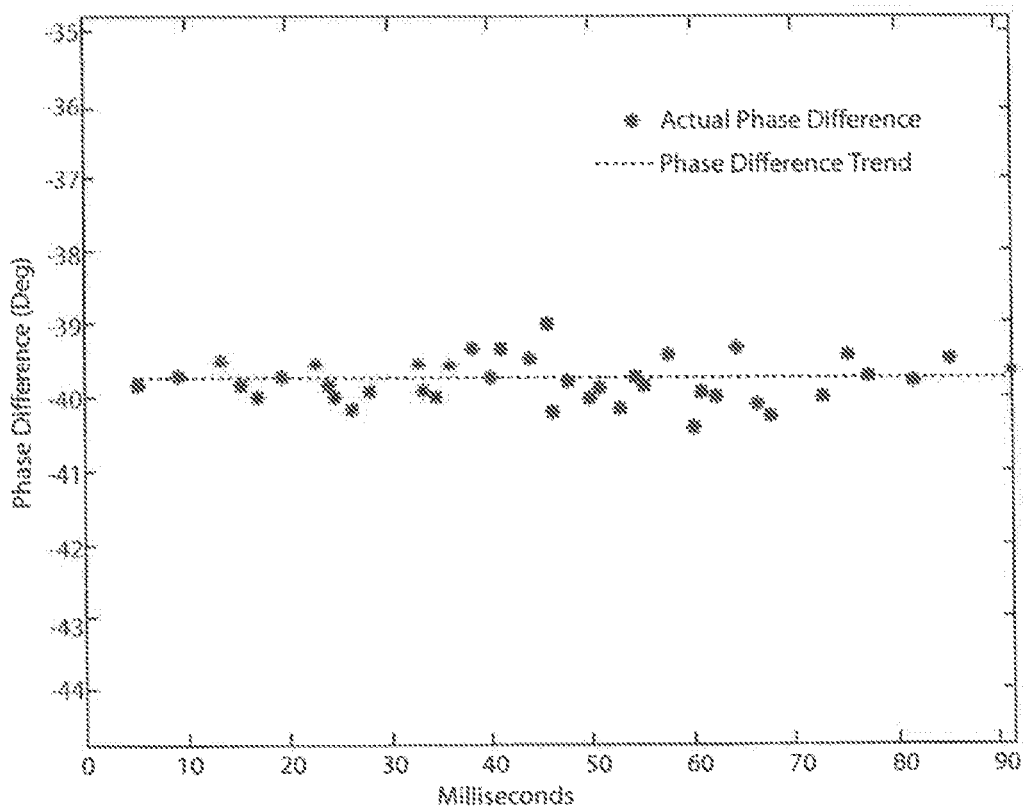
FIG. 23 is a plot of phase difference vs. time.

A variation on this embodiment is shown in FIGS. 22-23, in which an implantable device has multiple separated antennas 400 and phase difference from the antennas is measured. An external oscillator detects the phases φ1, φ2, φ3 and in one example operates at 300 MHz, giving a 0.36° phase shift for a 1 mm change in position.

The disclosure is not limited to the embodiments described but may be varied in construction and detail. The term "electrode" in this specification is intended to mean in the relevant context an electrode for either impedance or capacitive measurements or a passive electromagnetic transponder. Various embodiments may include one or more of any of the physical, electrode, of electronic features of any embodiment to achieve the desired result of monitoring a vessel dimension. It is also envisaged that the processor operations to perform re-construction or modelling of vessel dimensions based on parallelograms and/or ellipses may be performed based on monitoring chords by sensors other than electrodes, such as for example by way of ultrasonic transducers in which time of flight for echo signals or direct transfers across a vessel are monitored.

The invention claimed is:

1. A sensor system for monitoring parameters in a vessel, comprising:
    an implantable support structure configured to move with natural movement of the vessel wall;
    a plurality of pairs of electrodes coupled to the support structure and configured to be positioned circumferentially spaced around the vessel interior on, in or adjacent a wall of the vessel so as to move with natural movement of the vessel wall when the support structure moves therewith;
    a drive circuit configured to provide a drive signal to the electrodes,
    measurement circuitry configured to measure at least one of impedance and capacitance between at least two of the plurality of pairs of electrodes; and
    a communications circuit configured to wirelessly communicate date from the sensor;
    at least one reference electrode maintained at a fixed distance from one of the electrodes, wherein the measurement circuitry is configured to measure at least one of impedance or capacitance between said one of the electrodes and said reference electrode; and
    a signal processing circuit in at least one of the implantable sensor and an external console, wherein the signal processing circuit is configured to calculate distance between the electrode pairs based on the measured impedance or the measured capacitance, and wherein the signal processing circuit comprises a processor configured to execute instructions stored in a memory configured to perform one or more steps of:
    data correction with parallelogram edge and diagonal correction, by averaging opposed parallelogram sides;
    ellipse reconstruction to model a vessel shape, based on chordal lengths using parallelogram side calculations; and
    apply a correction to compensate for change from a round to elliptical cross-sectional shape of the vessel.

* * * * *